(12) United States Patent
Truckai

(10) Patent No.: US 9,814,520 B2
(45) Date of Patent: Nov. 14, 2017

(54) SYSTEM AND METHOD FOR ENDOMETRIAL ABLATION

(71) Applicant: Minerva Surgical, Inc., Redwood City, CA (US)

(72) Inventor: Csaba Truckai, Saratoga, CA (US)

(73) Assignee: Minerva Surgical, Inc., Redwood City, CA (US)

( * ) Notice: Subject to any disclaimer, the term of this patent is extended or adjusted under 35 U.S.C. 154(b) by 0 days.

(21) Appl. No.: 15/130,748

(22) Filed: Apr. 15, 2016

(65) Prior Publication Data

US 2016/0228179 A1    Aug. 11, 2016

Related U.S. Application Data

(63) Continuation of application No. 14/705,224, filed on May 6, 2015, now Pat. No. 9,339,330, which is a
(Continued)

(51) Int. Cl.
*A61B 18/18* (2006.01)
*A61B 18/14* (2006.01)
(Continued)

(52) U.S. Cl.
CPC ........ *A61B 18/1485* (2013.01); *A61B 18/042* (2013.01); *A61B 2018/0022* (2013.01); *A61B 2018/00083* (2013.01); *A61B 2018/00214* (2013.01); *A61B 2018/00232* (2013.01); *A61B 2018/00559* (2013.01); *A61B 2018/00577* (2013.01); *A61B 2018/00642* (2013.01); *A61B 2018/00678* (2013.01);
(Continued)

(58) Field of Classification Search
CPC .............. A61B 18/042; A61B 18/1485; A61B 2018/00083; A61B 2018/00214; A61B 2018/0022; A61B 2018/00232; A61B 2018/00559; A61B 2018/00577; A61B 2018/00642; A61B 2018/00678; A61B 2018/00744; A61B 2018/147; A61B 2090/064; A61B 2218/007
See application file for complete search history.

(56) References Cited

U.S. PATENT DOCUMENTS 4,611,604 A    9/1986   Botvidsson et al.
4,979,948 A    12/1990  Geddes et al.
(Continued)

OTHER PUBLICATIONS

Notice of allowance dated Jan. 15, 2016 for U.S. Appl. No. 14/705,224.
(Continued)

*Primary Examiner* — George Manuel
(74) *Attorney, Agent, or Firm* — Wilson, Sonsini, Goodrich & Rosati

(57) ABSTRACT

A wall of a uterus is ablated by expanding a structure in the uterus and applying energy across the wall of the structure into the uterine wall. An exterior surface of the structure conforms to an inner wall of the uterus, and the energy may cause vapor to collect between the wall and the structure. The vapor is released by providing a barrier to release which is inflated at a pressure above which the barrier at least partially collapses to allow the vapor to leave the uterus.

7 Claims, 26 Drawing Sheets

Related U.S. Application Data continuation of application No. 13/426,887, filed on Mar. 22, 2012, now Pat. No. 9,050,103.

(60) Provisional application No. 61/467,906, filed on Mar. 25, 2011.

(51) Int. Cl.
*A61B 18/04* (2006.01)
*A61B 90/00* (2016.01)
*A61B 18/00* (2006.01)

(52) U.S. Cl.
CPC ............... *A61B 2018/00744* (2013.01); *A61B 2018/147* (2013.01); *A61B 2090/064* (2016.02); *A61B 2218/007* (2013.01)

(56) References Cited

U.S. PATENT DOCUMENTS

| | | | |
|---|---|---|---|
| 5,191,883 A | 3/1993 | Lennox et al. | |
| 5,549,546 A | 8/1996 | Schneider et al. | |
| 5,769,880 A | 6/1998 | Truckai et al. | |
| 5,891,134 A | 4/1999 | Goble et al. | |
| 5,925,038 A | 7/1999 | Panescu et al. | |
| 6,041,260 A | 3/2000 | Stern et al. | |
| 6,149,620 A | 11/2000 | Baker et al. | |
| 6,296,639 B1 | 10/2001 | Truckai et al. | |
| 6,663,626 B2 | 12/2003 | Truckai et al. | |
| 6,736,811 B2 | 5/2004 | Panescu et al. | |
| 6,813,520 B2 | 11/2004 | Truckai et al. | |
| 7,371,231 B2 | 5/2008 | Rioux et al. | |
| 8,343,078 B2 * | 1/2013 | Toth | A61B 5/035 600/560 |
| 8,372,068 B2 | 2/2013 | Truckai | |
| 8,382,753 B2 | 2/2013 | Truckai | |
| 9,050,103 B2 | 6/2015 | Truckai | |
| 9,339,330 B2 | 5/2016 | Truckai | |
| 2005/0143728 A1 | 6/2005 | Sampson et al. | |
| 2005/0240211 A1 | 10/2005 | Sporri et al. | |
| 2008/0097425 A1 | 4/2008 | Truckai | |
| 2008/0167664 A1 | 7/2008 | Payne et al. | |
| 2009/0054892 A1 | 2/2009 | Rioux et al. | |
| 2009/0163908 A1 | 6/2009 | MacLean et al. | |
| 2010/0100091 A1 | 4/2010 | Truckai | |
| 2010/0100094 A1 | 4/2010 | Truckai | |
| 2012/0245583 A1 | 9/2012 | Truckai | |
| 2015/0250535 A1 | 9/2015 | Truckai | |

OTHER PUBLICATIONS

Notice of allowance dated Feb. 17, 2015 for U.S. Appl. No. 13/426,887.
Office action dated Jul. 18, 2014 for U.S. Appl. No. 13/426,887.
"Office action dated Oct. 6, 2015 for U.S. Appl. No. 14/705,224."
Third party observations dated Sep. 6, 2013 for EP Application No. 10830743.0.

* cited by examiner

SYSTEM AND METHOD FOR ENDOMETRIAL ABLATION

CROSS REFERENCE TO RELATED APPLICATIONS

This application is a continuation of U.S. patent application Ser. No. 14/705,224, filed May 6, 2015, which is a continuation of U.S. patent application Ser. No. 13/426,887, which was filed Mar. 22, 2012 and claims the benefit of Provisional Application No. 61/467,906, filed Mar. 25, 2011, the contents of which are incorporated herein by reference in its entirety.

BACKGROUND

1. Field of the Invention

The present invention relates to electrosurgical methods and devices for global endometrial ablation in a treatment of menorrhagia. More particularly, the present invention relates to applying radiofrequency current to endometrial tissue by means of capacitively coupling the current through an expandable, thin-wall dielectric member enclosing an ionized gas.

A variety of devices have been d or proposed for endometrial ablation. Of relevance to the present invention, a variety of radiofrequency ablation devices have been proposed including solid electrodes, balloon electrodes, metalized fabric electrodes, and the like. While often effective, many of the prior electrode designs have suffered from one or more deficiencies, such as relatively slow treatment times, incomplete treatments, non-uniform ablation depths, and risk of injury to adjacent organs.

For these reasons, it would be desirable to provide systems and methods that allow for endometrial ablation using radiofrequency current which is rapid, provides for controlled ablation depth and which reduce the risk of injury to adjacent organs. At least some of these objectives will be met by the invention described herein.

2. Description of the Background Art

U.S. Pat. Nos. 5,769,880; 6,296,639; 6,663,626; and 6,813,520 describe intrauterine ablation devices formed from a permeable mesh defining electrodes for the application of radiofrequency energy to ablate uterine tissue. U.S. Pat. No. 4,979,948 describes a balloon filled with an electrolyte solution for applying radiofrequency current to a mucosal layer via capacitive coupling. US 2008/097425, having common inventorship with the present application, describes delivering a pressurized flow of a liquid medium which carries a radiofrequency current to tissue, where the liquid is ignited into a plasma as it passes through flow orifices. U.S. Pat. No. 5,891,134 describes a radiofrequency heater within an enclosed balloon. U.S. Pat. No. 6,041,260 describes radiofrequency electrodes distributed over the exterior surface of a balloon which is inflated in a body cavity to be treated. U.S. Pat. No. 7,371,231 and US 2009/054892 describe a conductive balloon having an exterior surface which acts as an electrode for performing endometrial ablation. U.S. Pat. No. 5,191,883 describes bipolar heating of a medium within a balloon for thermal ablation. U.S. Pat. No. 6,736,811 and U.S. Pat. No. 5,925,038 show an inflatable conductive electrode.

SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention provides methods for ablating a wall of a uterus by expanding a structure in the uterus and applying energy across the wall of the structure into the uterine wall. The exterior surface conforms to an inner wall of the uterus, and the energy may be transferred into the wall in any conventional manner. In the exemplary embodiments described below, the structure which is expanded comprises a dielectric material, and the energy is delivered by generating a plasma in a low pressure gas within the structure and inductively coupling the energy across the dielectric wall.

Of particular interest to the present invention, a vapor will often be released from the tissue of the uterine cavity and can collect in pockets between an exterior surface of the expanded structure and an inner wall of the uterus. The presence of such collected vapors can reduce the efficiency of energy transfer into the uterine wall and is therefore undesirable.

The present invention provides methods and systems for releasing vapor from the uterine cavity, particularly vapor which has collected in pockets as described above, whenever the pressure of the vapor exceeds a preselected level. Typically, the vapor will be released whenever the pressure exceeds a pressure in the range from 10 mm Hg to 100 mm Hg, typically being in the range from 25 mm Hg to 75 mm Hg.

While the vapor release could be effected by a variety of valves and feedback control systems, it will usually be desirable to use a simpler system which releases the pressure based on a balancing of an internal pressure and an external pressure, as will be described in more detail below. For example, releasing can be effected by inflating a barrier in a vapor release path between the uterine cavity and an exterior where the barrier is inflated at the desired release pressure. Thus, whenever the pressure of vapor within the uterine cavity exceeds this preselected release pressure, the barrier will open and the vapor will be bled from the cavity until the pressure falls below the preselected level. In specific examples, the barrier may comprise an inflatable balloon which is disposed in a release path through the cervix and vaginal canal. In other cases, the barrier may comprise a portion of the expandable structure which contains the plasma generating the energy. In still other case, the plasma within the expandable structure will be maintained at the preselected release pressure.

In many embodiments, the vapor will be released through a path defined by a lumen in a probe which carries the energy delivery structure. The lumen will be open at a distal end to the interior of the uterine cavity in order to receive vapor when the pressure exceeds the preselected level. The balloon or other inflatable barrier will typically be disposed in a distal end of a lumen, where a pressure in excess of the inflation pressure deflects the balloon or other barrier inwardly to allow the vapor to flow through the newly created path into the lumen.

In other aspects of the present invention, an endometrial ablation device comprises a probe, an expandable energy delivery structure coupled to a distal end of the probe, and an inflatable element disposed on the probe to control flow of vapor from a uterine cavity into a probe lumen. The probe typically is adapted for trans-vaginal introduction into the uterus and includes a proximal end, a distal end, and a vapor release lumen extending from the proximal end to the distal end. The expandable structure is coupled to the distal end of the probe and is typically adapted to receive argon or other low pressure gas suitable for initiating a plasma in order to deliver energy across the wall of the expandable structure by inductive coupling. The structure will be further adapted to conform to an inner wall of the uterus, and so long as the structure is in close contact with the uterine wall, energy delivery can be efficiently achieved.

The inflatable element is typically disposed in the vapor release lumen, and its distal end and will be inflated to a pressure substantially equal to the desired pressure at which vapor generated within the uterine cavity is to be released. The inflatable element may be a balloon structure which is independently inflatable, i.e. the expandable structure is separately inflatable. Alternatively, the inflatable device may comprise a proximal portion of the expandable structure. When the inflatable device comprises a separate balloon structure, the ablation device typically includes a separate inflation source coupled to deliver an inflation medium to the inflation element, which medium is in addition to the low pressure gas use for generating the plasma.

Typically, the inflation source and/or plasma source will be adapted to inflate the inflatable element at pressure in the range from 10 mm Hg to 100 mm Hg, usually being in the range for 25 mm Hg to 75 mm Hg.

In certain embodiment, a distal end of the probe which surrounds the inflatable element maybe slotted or otherwise split in order to facilitate expansion of the probe while still protecting the surrounding issues.

For a fuller understanding of the nature and advantages of the present invention, reference should be made to the ensuing detailed description and accompanying drawings.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE INVENTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

In general, an electrosurgical ablation system is described herein that comprises an elongated introducer member for accessing a patient's uterine cavity with a working end that deploys an expandable thin-wall dielectric structure containing an electrically non-conductive gas as a dielectric. In one embodiment, an interior chamber of the thin-wall dielectric structure contains a circulating neutral gas such as argon. An RF power source provides current that is coupled to the neutral gas flow by a first polarity electrode disposed within the interior chamber and a second polarity electrode at an exterior of the working end. The gas flow, which is converted to a conductive plasma by an electrode arrangement, functions as a switching mechanism that permits current flow to engaged endometrial tissue only when the voltage across the combination of the gas, the thin-wall dielectric structure and the engaged tissue reaches a threshold that causes capacitive coupling across the thin-wall dielectric material. By capacitively coupling current to tissue in this manner, the system provides a substantially uniform tissue effect within all tissue in contact with the expanded dielectric structure. Further, the invention allows the neutral gas to be created contemporaneously with the capacitive coupling of current to tissue.

In general, this disclosure may use the terms "plasma", "conductive gas" and "ionized gas" interchangeably. A plasma consists of a state of matter in which electrons in a neutral gas are stripped or "ionized" from their molecules or atoms. Such plasmas can be formed by application of an electric field or by high temperatures. In a neutral gas, electrical conductivity is non-existent or very low. Neutral gases act as a dielectric or insulator until the electric field reaches a breakdown value, freeing the electrons from the atoms in an avalanche process thus forming a plasma. Such a plasma provides mobile electrons and positive ions, and acts as a conductor which supports electric currents and can form spark or arc. Due to their lower mass, the electrons in a plasma accelerate more quickly in response to an electric field than the heavier positive ions, and hence carry the bulk of the current.

Figure 1:
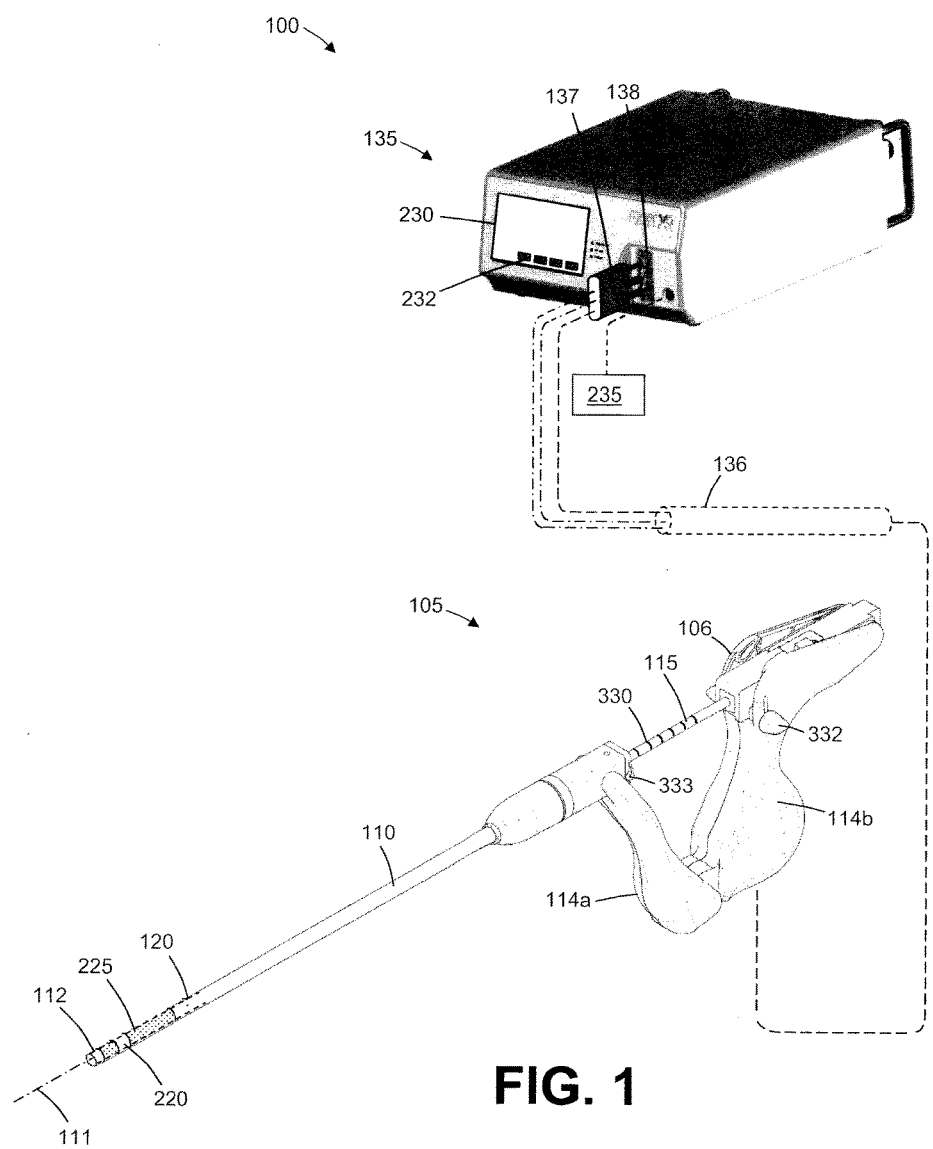
FIG. 1 is a perspective view of an ablation system corresponding to the invention, including a hand-held electrosurgical device for endometrial ablation, RF power source, gas source and controller.
Figure 2:
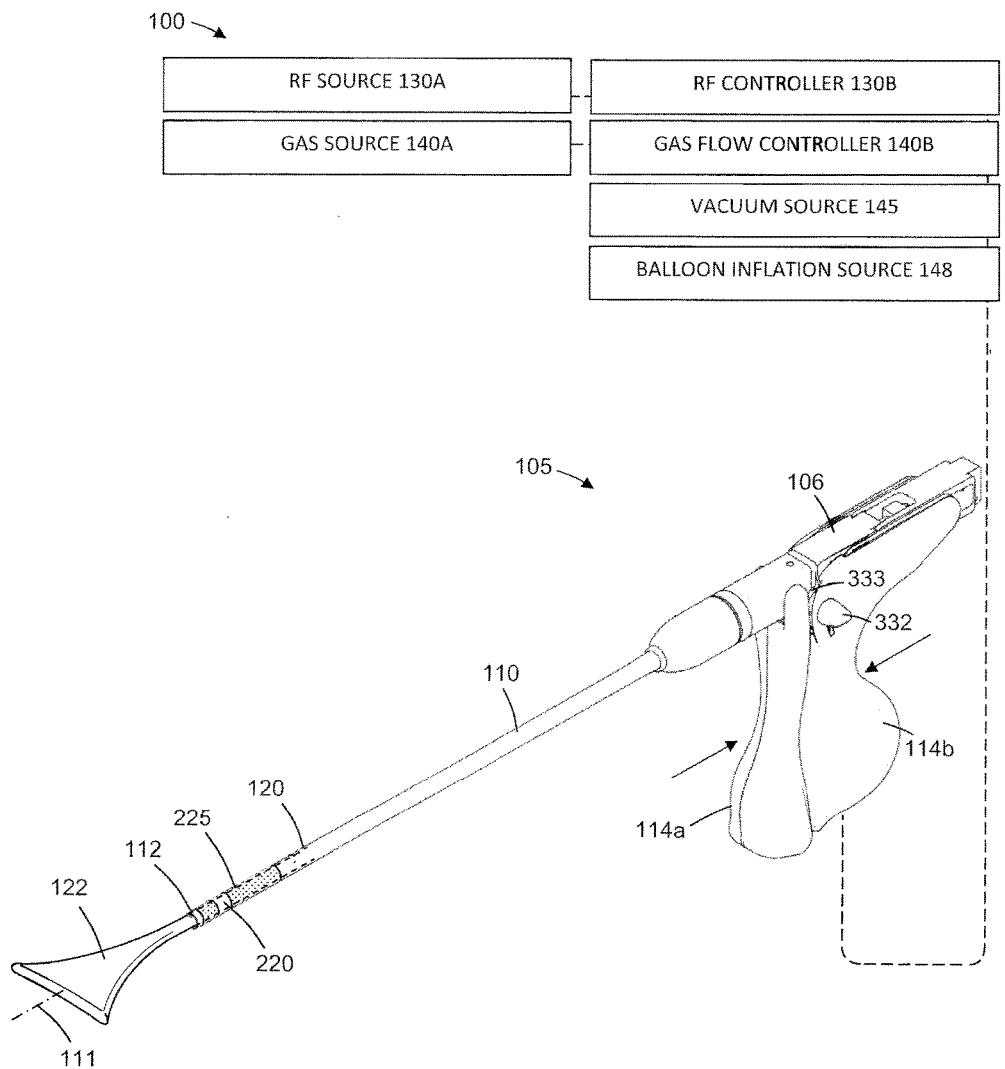
FIG. 2 is a view of the hand-held electrosurgical device of FIG. 1 with a deployed, expanded thin-wall dielectric structure.

FIG. 1 depicts one embodiment of an electrosurgical ablation system 100 configured for endometrial ablation. The system 100 includes a hand-held apparatus 105 with a proximal handle 106 shaped for grasping with a human hand that is coupled to an elongated introducer sleeve 110 having axis 111 that extends to a distal end 112. The introducer sleeve 110 can be fabricated of a thin-wall plastic, composite, ceramic or metal in a round or oval cross-section having a diameter or major axis ranging from about 4 mm to 8 mm in at least a distal portion of the sleeve that accesses the uterine cavity. The handle 106 is fabricated of an electrically insulative material such as a molded plastic with a pistol-grip having first and second portions, 114a and 114b, that can be squeezed toward one another to translate an elongated translatable sleeve 115 which is housed in a bore 120 in the elongated introducer sleeve 110. By actuating the first and second handle portions, 114a and 114b, a working end 122 can be deployed from a first retracted position (FIG. 1) in the distal portion of bore 120 in introducer sleeve 110 to an extended position as shown in FIG. 2. In FIG. 2, it can be seen that the first and second handle portions, 114a and 114b, are in a second actuated position with the working end 122 deployed from the bore 120 in introducer sleeve 110.

Figure 3:
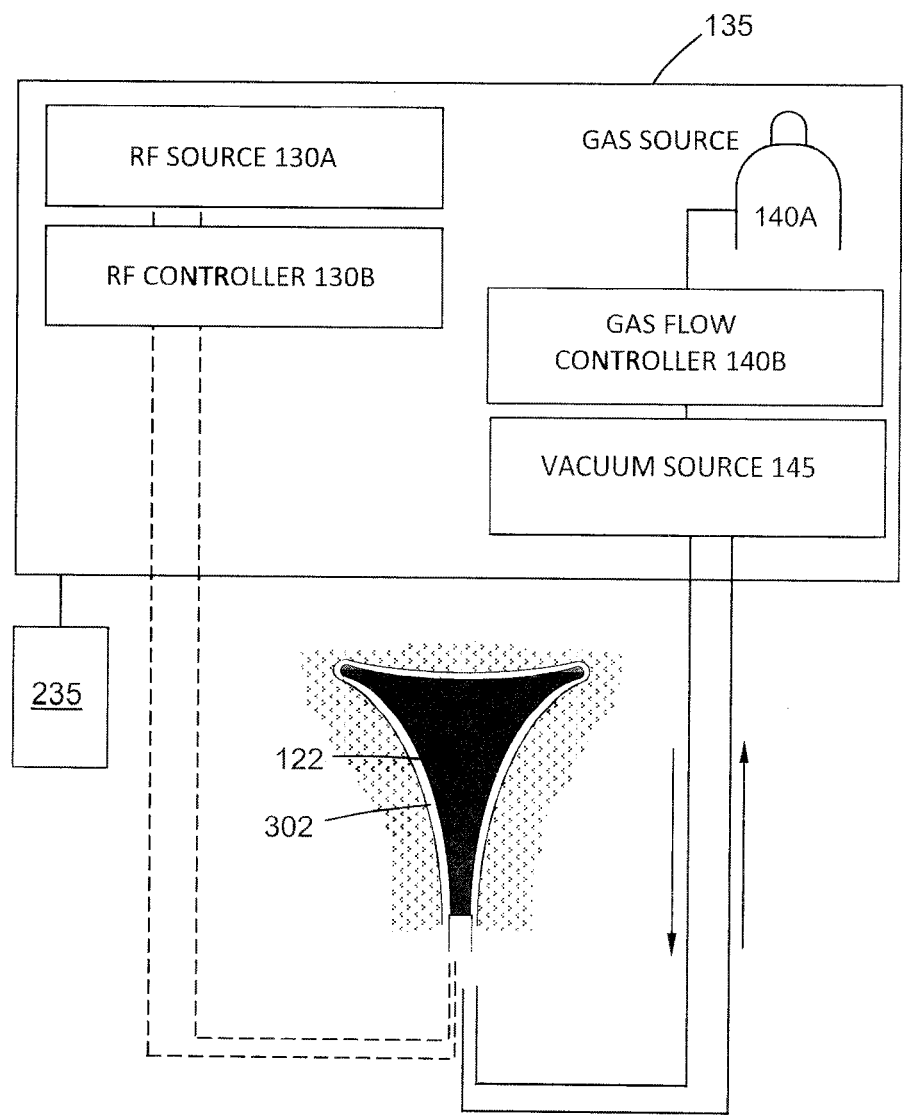
FIG. 3 is a block diagram of components of one electrosurgical system corresponding to the invention.

FIGS. 2 and 3 shows that ablation system 100 includes an RF energy source 130A and RF controller 130B in a control unit 135. The RF energy source 130A is connected to the hand-held device 105 by a flexible conduit 136 with a plug-in connector 137 configured with a gas inflow channel, a gas outflow channel, and first and second electrical leads for connecting to receiving connector 138 in the control unit 135. The control unit 135, as will be described further below in FIGS. 3 and 4, further comprises a neutral gas inflow source 140A, gas flow controller 140B and optional vacuum or negative pressure source 145 to provide controlled gas inflows and gas outflows to and from the working end 122. The control unit 135 further includes a balloon inflation source 148 for inflating an expandable sealing balloon 225 carried on introducer sleeve 110 as described further below.

Referring to FIG. 2, the working end 122 includes a flexible, thin-wall member or structure 150 of a dielectric material that when expanded has a triangular shape configured for contacting the patient's endometrial lining that is targeted for ablation. In one embodiment as shown in FIGS. 2, 5 and 6, the dielectric structure 150 comprises a thin-wall material such as silicone with a fluid-tight interior chamber 152.

In an embodiment, an expandable-collapsible frame assembly 155 is disposed in the interior chamber. Alternatively, the dielectric structure may be expanded by a neutral gas without a frame, but using a frame offers a number of advantages. First, the uterine cavity is flattened with the opposing walls in contact with one another. Expanding a balloon-type member may cause undesirable pain or spasms. For this reason, a flat structure that is expanded by a frame is better suited for deployment in the uterine cavity. Second, in embodiments herein, the neutral gas is converted to a conductive plasma at a very low pressure controlled by gas inflows and gas outflows—so that any pressurization of a balloon-type member with the neutral gas may exceed a desired pressure range and would require complex controls of gas inflows and gas outflows. Third, as described below, the frame provides an electrode for contact with the neutral gas in the interior chamber 152 of the dielectric structure 150, and the frame 155 extends into all regions of the interior chamber to insure electrode exposure to all regions of the neutral gas and plasma. The frame 155 can be constructed of any flexible material with at least portions of the frame functioning as spring elements to move the thin-wall structure 150 from a collapsed configuration (FIG. 1) to an expanded, deployed configuration (FIG. 2) in a patient's uterine cavity. In one embodiment, the frame 155 comprises stainless steel elements 158a, 158b and 160a and 160b that function akin to leaf springs. The frame can be a stainless steel such as 316 SS, 17A SS, 420 SS, 440 SS or the frame can be a NiTi material. The frame preferably extends along a single plane, yet remains thin transverse to the plane, so that the frame may expand into the uterine cavity. The frame elements can have a thickness ranging from about 0.005" to 0.025". As can be seen in FIGS. 5 and 6, the proximal ends 162a and 162b of spring elements 158a, 158b are fixed (e.g., by welds 164) to the distal end 165 of sleeve member 115. The proximal ends 166a and 166b of spring elements 160a, 160b are welded to distal portion 168 of a secondary translatable sleeve 170 that can be extended from bore 175 in translatable sleeve 115. The secondary translatable sleeve 170 is dimensioned for a loose fit in bore 175 to allow gas flows within bore 175. FIGS. 5 and 6 further illustrate the distal ends 176a and 176b of spring elements 158a, 158b are welded to distal ends 178a and 178b of spring elements 160a and 160b to thus provide a frame 155 that can be moved from a linear shape (see FIG. 1) to an expanded triangular shape (FIGS. 5 and 6).

As will be described further below, the bore 175 in sleeve 115 and bore 180 in secondary translatable sleeve 170 function as gas outflow and gas inflow lumens, respectively. It should be appreciated that the gas inflow lumen can comprise any single lumen or plurality of lumens in either sleeve 115 or sleeve 170 or another sleeve, or other parts of the frame 155 or the at least one gas flow lumen can be formed into a wall of dielectric structure 150. In FIGS. 5, 6 and 7 it can be seen that gas inflows are provided through bore 180 in sleeve 170, and gas outflows are provided in bore 175 of sleeve 115. However, the inflows and outflows can be also be reversed between bores 175 and 180 of the various sleeves. FIGS. 5 and 6 further show that a rounded bumper element 185 is provided at the distal end of sleeve 170 to insure that no sharp edges of the distal end of sleeve 170 can contact the inside of the thin dielectric wall 150. In one embodiment, the bumper element 185 is silicone, but it could also comprise a rounded metal element. FIGS. 5 and 6 also show that a plurality of gas inflow ports 188 can be provided along a length of in sleeve 170 in chamber 152, as well as a port 190 in the distal end of sleeve 170 and bumper element 185. The sectional view of FIG. 7 also shows the gas flow passageways within the interior of introducer sleeve 110.

Figure 5:
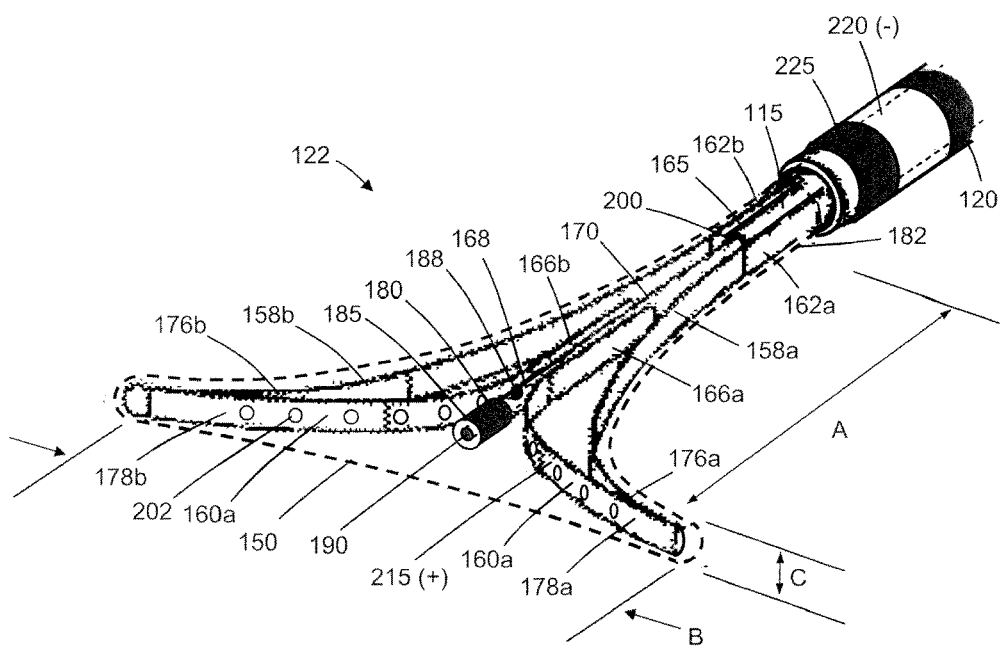
FIG. 5 is an enlarged perspective view of the expanded thin-wall dielectric structure, showing an expandable-collapsible frame with the thin dielectric wall in phantom view.
Figure 6:
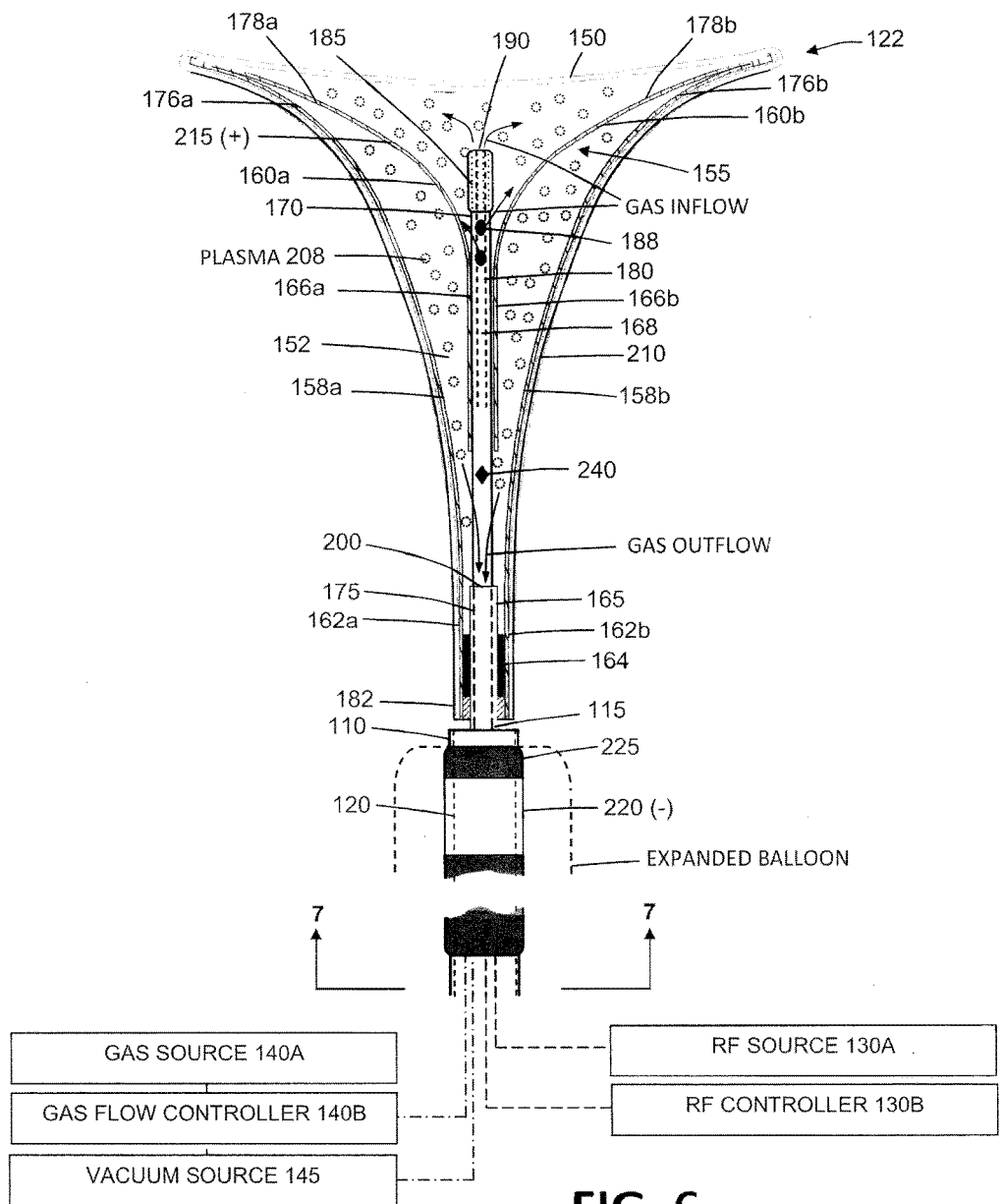
FIG. 6 is a partial sectional view of the expanded thin-wall dielectric structure of FIG. 5 showing (i) translatable members of the expandable-collapsible frame a that move the structure between collapsed and (ii) gas inflow and outflow lumens.
Figure 7:
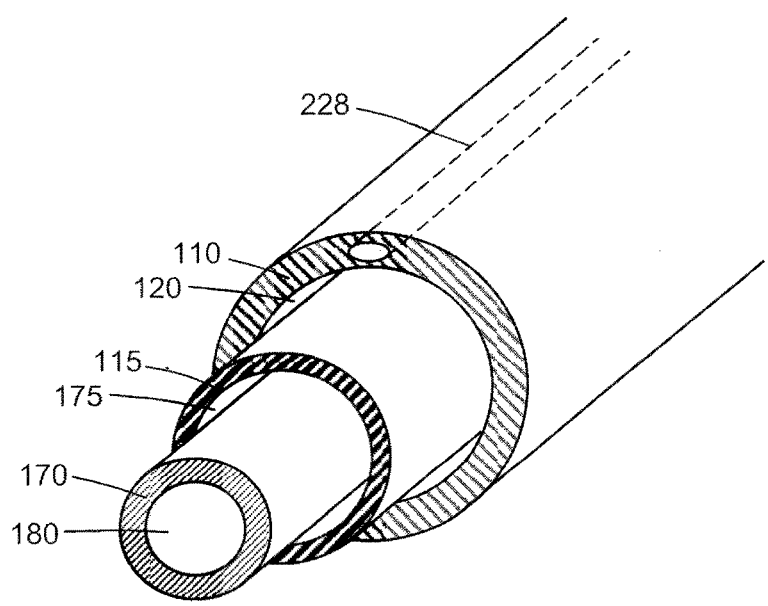
FIG. 7 is a sectional view of an introducer sleeve showing various lumens of the introducer sleeve taken along line 7-7 of FIG. 6.

It can be understood from FIGS. 1, 2, 5 and 6 that actuation of first and second handle portions, 114a and 114b, (i) initially causes movement of the assembly of sleeves 115 and 170 relative to bore 120 of introducer sleeve 110, and (ii) secondarily causes extension of sleeve 170 from bore 175 in sleeve 115 to expand the frame 155 into the triangular shape of FIG. 5. The dimensions of the triangular shape are suited for a patient uterine cavity, and for example can have an axial length A ranging from 4 to 10 cm and a maximum width B at the distal end ranging from about 2 to 5 cm. In one embodiment, the thickness C of the thin-wall structure 150 can be from 1 to 4 mm as determined by the dimensions of spring elements 158a, 158b, 160a and 160b of frame assembly 155. It should be appreciated that the frame assembly 155 can comprise round wire elements, flat spring elements, of any suitable metal or polymer that can provide opening forces to move thin-wall structure 150 from a collapsed configuration to an expanded configuration within the patient uterus. Alternatively, some elements of the frame 155 can be spring elements and some elements can be flexible without inherent spring characteristics.

As will be described below, the working end embodiment of FIGS. 2, 5 and 6 has a thin-wall structure 150 that is formed of a dielectric material such as silicone that permits capacitive coupling of current to engaged tissue while the frame assembly 155 provides structural support to position the thin-wall structure 150 against tissue. Further, gas inflows into the interior chamber 152 of the thin-wall structure can assist in supporting the dielectric wall so as to contact endometrial tissue. The dielectric thin-wall structure 150 can be free from fixation to the frame assembly 155, or can be bonded to an outward-facing portion or portions of frame elements 158a and 158b. The proximal end 182 of thin-wall structure 150 is bonded to the exterior of the distal end of sleeve 115 to thus provide a sealed, fluid-tight interior chamber 152 (FIG. 5).

In one embodiment, the gas inflow source 140A comprises one or more compressed gas cartridges that communicate with flexible conduit 136 through plug-in connector 137 and receiving connector 138 in the control unit 135 (FIGS. 1-2). As can be seen in FIGS. 5-6, the gas inflows from source 140A flow through bore 180 in sleeve 170 to open terminations 188 and 190 therein to flow into interior chamber 152. A vacuum source 145 is connected through conduit 136 and connector 137 to allow circulation of gas flow through the interior chamber 152 of the thin-wall dielectric structure 150. In FIGS. 5 and 6, it can be seen that gas outflows communicate with vacuum source 145 through open end 200 of bore 175 in sleeve 115. Referring to FIG. 5, it can be seen that frame elements 158a and 158b are configured with a plurality of apertures 202 to allow for gas flows through all interior portions of the frame elements, and thus gas inflows from open terminations 188, 190 in bore 180 are free to circulated through interior chamber 152 to return to an outflow path through open end 200 of bore 175 of sleeve 115. As will be described below (see FIGS. 3-4), the gas inflow source 140A is connected to a gas flow or circulation controller 140B which controls a pressure regulator 205 and also controls vacuum source 145 which is adapted for assisting in circulation of the gas. It should be appreciated that the frame elements can be configured with apertures, notched edges or any other configurations that allow for effective circulation of a gas through interior chamber 152 of the thin-wall structure 150 between the inflow and outflow passageways.

Now turning to the electrosurgical aspects of the invention, FIGS. 5 and 6 illustrate opposing polarity electrodes of the system 100 that are configured to convert a flow of neutral gas in chamber 152 into a plasma 208 (FIG. 6) and to allow capacitive coupling of current through a wall 210 of the thin-wall dielectric structure 150 to endometrial tissue in contact with the wall 210. The electrosurgical methods of capacitively coupling RF current across a plasma 208 and dielectric wall 210 are described in U.S. patent application Ser. No. 12/541,043; filed Aug. 13, 2009 and U.S. application Ser. No. 12/541,050, referenced above. In FIGS. 5 and 6, the first polarity electrode 215 is within interior chamber 152 to contact the neutral gas flow and comprises the frame assembly 155 that is fabricated of an electrically conductive stainless steel. In another embodiment, the first polarity electrode can be any element disposed within the interior chamber 152, or extendable into interior chamber 152. The first polarity electrode 215 is electrically coupled to sleeves 115 and 170 which extends through the introducer sleeve 110 to handle 106 and conduit 136 and is connected to a first pole of the RF source energy source 130A and controller 130B. A second polarity electrode 220 is external of the internal chamber 152 and in one embodiment the electrode is spaced apart from wall 210 of the thin-wall dielectric structure 150. In one embodiment as depicted in FIGS. 5 and 6, the second polarity electrode 220 comprises a surface element of an expandable balloon member 225 carried by introducer sleeve 110. The second polarity electrode 220 is coupled by a lead (not shown) that extends through the introducer sleeve 110 and conduit 136 to a second pole of the RF source 130A. It should be appreciated that second polarity electrode 220 can be positioned on sleeve 110 or can be attached to surface portions of the expandable thin-wall dielectric structure 150, as will be described below, to provide suitable contact with body tissue to allow the electrosurgical ablation of the method of the invention. The second polarity electrode 220 can comprise a thin conductive metallic film, thin metal wires, a conductive flexible polymer or a polymeric positive temperature coefficient material. In one embodiment depicted in FIGS. 5 and 6, the expandable member 225 comprises a thin-wall compliant balloon having a length of about 1 cm to 6 cm that can be expanded to seal the cervical canal. The balloon 225 can be inflated with a gas or liquid by any inflation source 148, and can comprise a syringe mechanism controlled manually or by control unit 135. The balloon inflation source 148 is in fluid communication with an inflation lumen 228 in introducer sleeve 110 that extends to an inflation chamber of balloon 225 (see FIG. 7).

Referring back to FIG. 1, the control unit 135 can include a display 230 and touch screen or other controls 232 for setting and controlling operational parameters such as treatment time intervals, treatment algorithms, gas flows, power levels and the like. Suitable gases for use in the system include argon, other noble gases and mixtures thereof. In one embodiment, a footswitch 235 is coupled to the control unit 135 for actuating the system.

Figure 4:
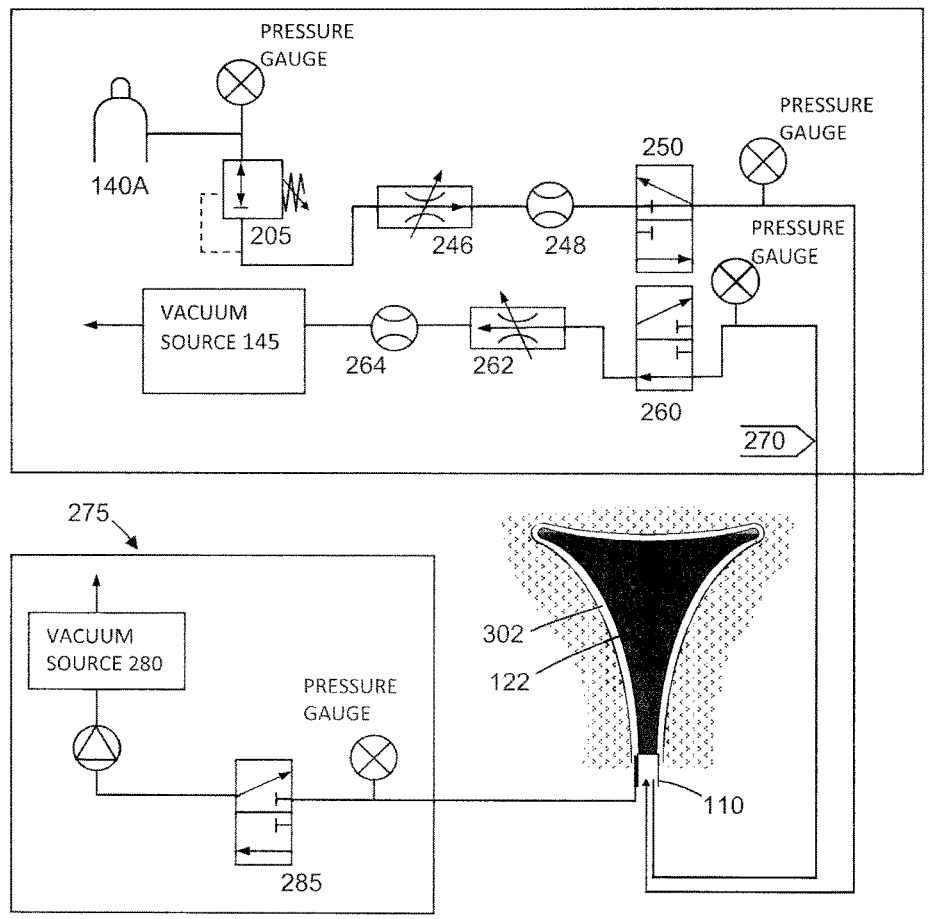
FIG. 4 is a block diagram of the gas flow components of the electrosurgical system of FIG. 1.

The box diagrams of FIGS. 3 and 4 schematically depict the system 100, subsystems and components that are configured for an endometrial ablation system. In the box diagram of FIG. 3, it can be seen that RF energy source 130A and circuitry is controlled by a controller 130B. The system can include feedback control systems that include signals relating to operating parameters of the plasma in interior chamber 152 of the dielectric structure 150. For example, feedback signals can be provided from at least one temperature sensor 240 in the interior chamber 152 of the dielectric structure 150, from a pressure sensor within, or in communication, with interior chamber 152, and/or from a gas flow rate sensor in an inflow or outflow channel of the system. FIG. 4 is a schematic block diagram of the flow control components relating to the flow of gas media through the system 100 and hand-held device 105. It can be seen that a pressurized gas source 140A is linked to a downstream pressure regulator 205, an inflow proportional valve 246, flow meter 248 and normally closed solenoid valve 250. The valve 250 is actuated by the system operator which then allows a flow of a neutral gas from gas source 140A to circulate through flexible conduit 136 and the device 105. The gas outflow side of the system includes a normally open solenoid valve 260, outflow proportional valve 262 and flow meter 264 that communicate with vacuum pump or source 145. The gas can be exhausted into the environment or into a containment system. A temperature sensor 270 (e.g., thermocouple) is shown in FIG. 4 that is configured for monitoring the temperature of outflow gases. FIG. 4 further depicts an optional subsystem 275 which comprises a vacuum source 280 and solenoid valve 285 coupled to the controller 140B for suctioning steam from a uterine cavity 302 at an exterior of the dielectric structure 150 during a treatment interval. As can be understood from FIG. 4, the flow passageway from the uterine cavity 302 can be through bore 120 in sleeve 110 (see FIGS. 2, 6 and 7) or another lumen in a wall of sleeve 110 can be provided.

FIGS. 8A-8D schematically illustrate a method of the invention wherein (i) the thin-wall dielectric structure 150 is deployed within a patient uterus and (ii) RF current is applied to a contained neutral gas volume in the interior chamber 152 to contemporaneously create a plasma 208 in the chamber and capacitively couple current through the thin dielectric wall 210 to apply ablative energy to the endometrial lining to accomplish global endometrial ablation.

Figure 8A:
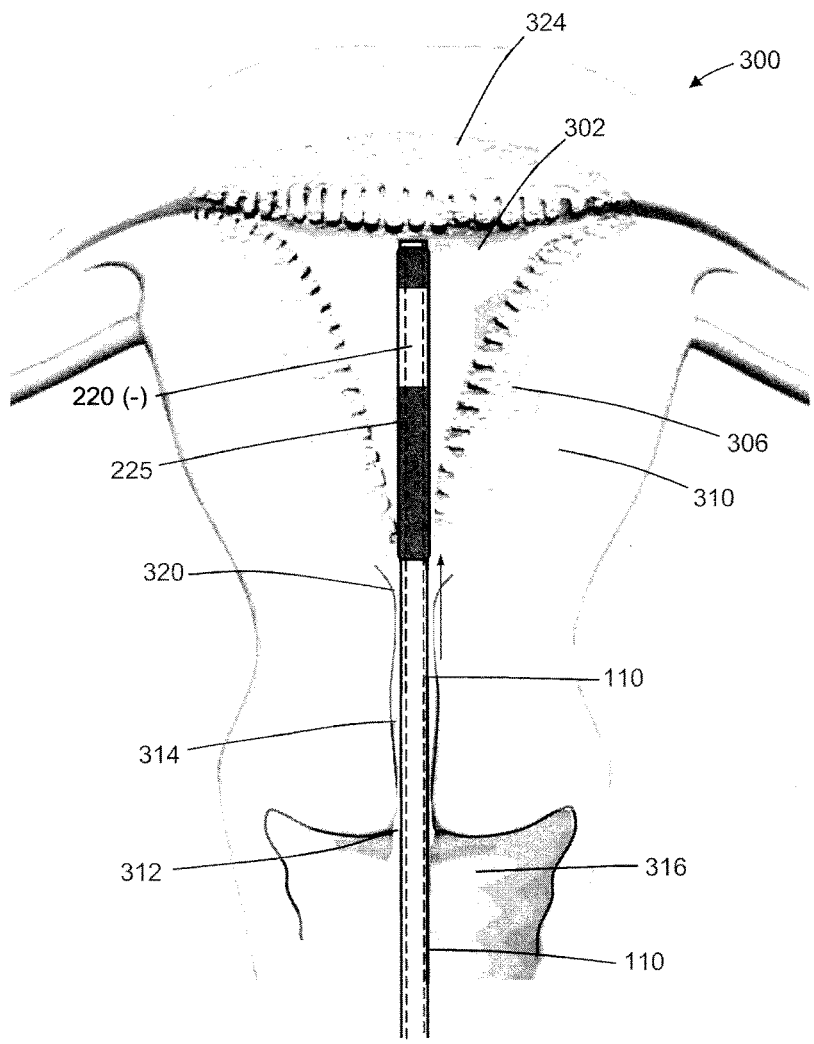
FIG. 8A is an enlarged schematic view of an aspect of a method of the invention illustrating the step introducing an introducer sleeve into a patient's uterus.

More in particular, FIG. 8A illustrates a patient uterus 300 with uterine cavity 302 surrounded by endometrium 306 and myometrium 310. The external cervical os 312 is the opening of the cervix 314 into the vagina 316. The internal os or opening 320 is a region of the cervical canal that opens to the uterine cavity 302. FIG. 8A depicts a first step of a method of the invention wherein the physician has introduced a distal portion of sleeve 110 into the uterine cavity 302. The physician gently can advance the sleeve 110 until its distal tip contacts the fundus 324 of the uterus. Prior to insertion of the device, the physician can optionally introduce a sounding instrument into the uterine cavity to determine uterine dimensions, for example from the internal os 320 to fundus 324.

Figure 8B:
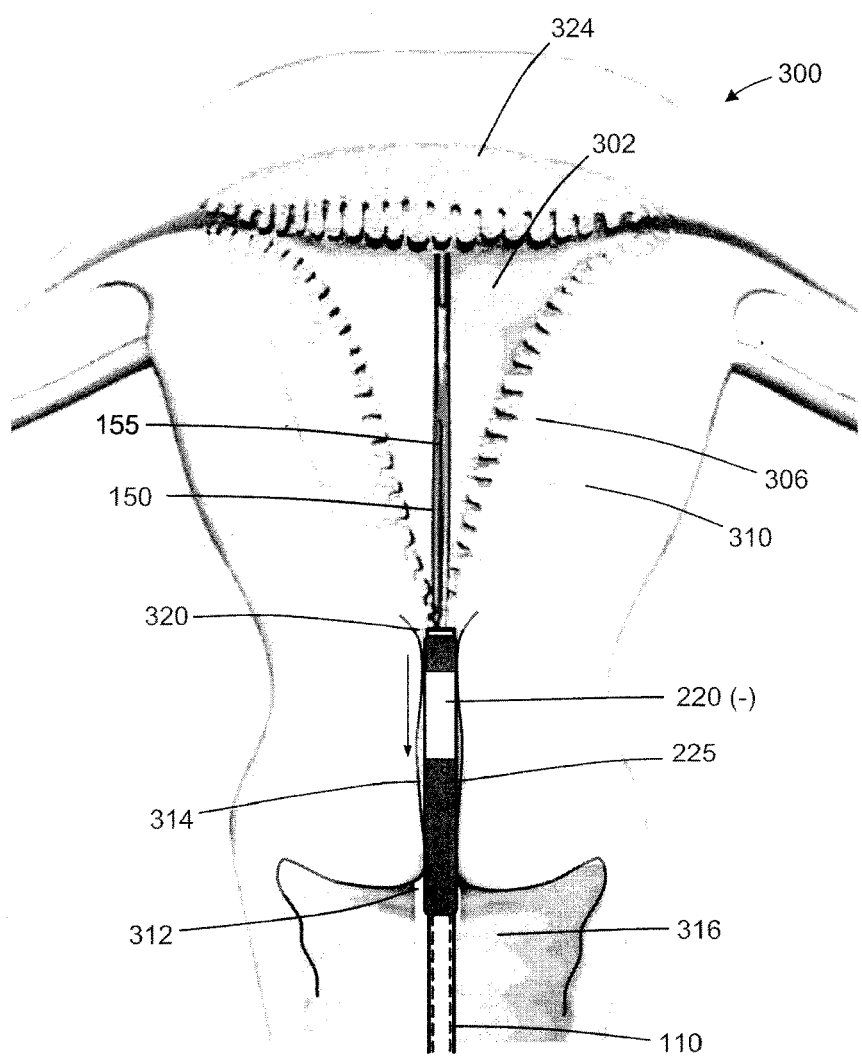
FIG. 8B is a schematic view of a subsequent step of retracting the introducer sleeve to expose a collapsed thin-wall dielectric structure and internal frame in the uterine cavity.

FIG. 8B illustrates a subsequent step of a method of the invention wherein the physician begins to actuate the first and second handle portions, 114a and 114b, and the introducer sleeve 110 retracts in the proximal direction to expose the collapsed frame 155 and thin-wall structure 150 within the uterine cavity 302. The sleeve 110 can be retracted to expose a selected axial length of thin-wall dielectric structure 150, which can be determined by markings 330 on sleeve 115 (see FIG. 1) which indicate the axial travel of sleeve 115 relative to sleeve 170 and thus directly related to the length of deployed thin-wall structure 150. FIG. 2 depicts the handle portions 114a and 114b fully approximated thus deploying the thin-wall structure to its maximum length.

Figure 8C:
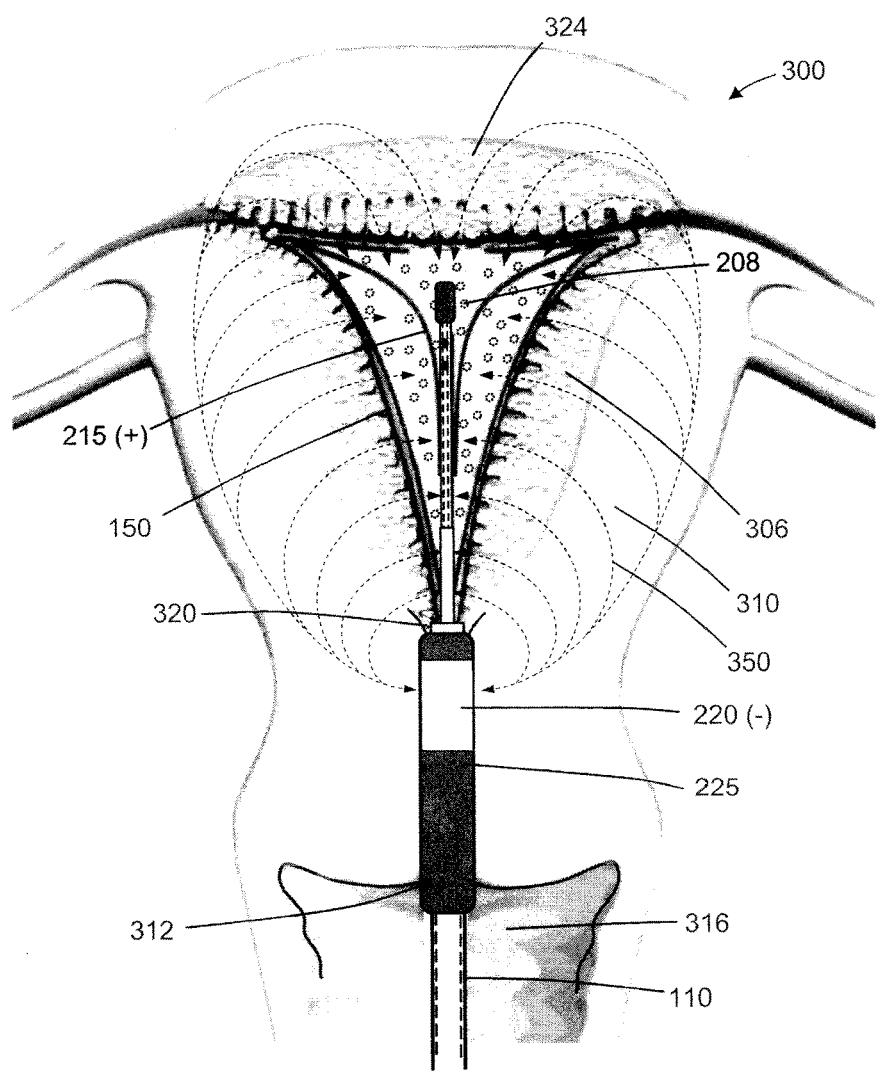
FIG. 8C is a schematic view of subsequent steps of the method, including, (i) actuating the internal frame to move the a collapsed thin-wall dielectric structure to an expanded configuration, (ii) inflating a cervical-sealing balloon carried on the introducer sleeve, and (iii) actuating gas flows and applying RF energy to contemporaneously ionize the gas in the interior chamber and cause capacitive coupling of current through the thin-wall dielectric structure to cause ohmic heating in the engaged tissue indicated by current flow paths.

FIG. 8C illustrates several subsequent steps of a method of the invention. FIG. 8C first depicts the physician continuing to actuate the first and second handle portions, 114a and 114b, which further actuates the frame 155 (see FIGS. 5-6) to expand the frame 155 and thin-wall structure 150 to a deployed triangular shape to contact the patient's endometrial lining 306. The physician can slightly rotate and move the expanding dielectric structure 150 back and forth as the structure is opened to insure it is opened to the desired extent. In performing this step, the physician can actuate handle portions, 114a and 114b, a selected degree which causes a select length of travel of sleeve 170 relative to sleeve 115 which in turn opens the frame 155 to a selected degree. The selected actuation of sleeve 170 relative to sleeve 115 also controls the length of dielectric structure deployed from sleeve 110 into the uterine cavity. Thus, the thin-wall structure 150 can be deployed in the uterine cavity with a selected length, and the spring force of the elements of frame 155 will open the structure 150 to a selected triangular shape to contact or engage the endometrium 306. In one embodiment, the expandable thin-wall structure 150 is urged toward and maintained in an open position by the spring force of elements of the frame 155. In the embodiment depicted in FIGS. 1 and 2, the handle 106 includes a locking mechanism with finger-actuated sliders 332 on either side of the handle that engage a grip-lock element against a notch in housing 333 coupled to introducer sleeve 110 (FIG. 2) to lock sleeves 115 and 170 relative to introducer sleeve 110 to maintain the thin-wall dielectric structure 150 in the selected open position.

FIG. 8C further illustrates the physician expanding the expandable balloon structure 225 from inflation source 148 to thus provide an elongated sealing member to seal the cervix 314 outward from the internal os 320. Following deployment of the thin-wall structure 150 and balloon 225 in the cervix 314, the system 100 is ready for the application of RF energy to ablate endometrial tissue 306. FIG. 8C next depicts the actuation of the system 100, for example, by actuating footswitch 235, which commences a flow of neutral gas from source 140A into the interior chamber 152 of the thin-wall dielectric structure 150. Contemporaneous with, or after a selected delay, the system's actuation delivers RF energy to the electrode arrangement which includes first polarity electrode 215 (+) of frame 155 and the second polarity electrode 220 (−) which is carried on the surface of expandable balloon member 225. The delivery of RF energy delivery will instantly convert the neutral gas in interior chamber 152 into conductive plasma 208 which in turn results in capacitive coupling of current through the dielectric wall 210 of the thin-wall structure 150 resulting in ohmic heating of the engaged tissue. FIG. 8C schematically illustrates the multiplicity of RF current paths 350 between the plasma 208 and the second polarity electrode 220 through the dielectric wall 210. By this method, it has been found that ablation depths of three mm to six mm or more can be accomplished very rapidly, for example in 60 seconds to 120 seconds dependent upon the selected voltage and other operating parameters. In operation, the voltage at which the neutral gas inflow, such as argon, becomes conductive (i.e., converted in part into a plasma) is dependent upon a number of factors controlled by the controllers 130B and 140B, including the pressure of the neutral gas, the volume of interior chamber 152, the flow rate of the gas through the chamber 152, the distance between electrode 210 and interior surfaces of the dielectric wall 210, the dielectric constant of the dielectric wall 210 and the selected voltage applied by the RF source 130, all of which can be optimized by experimentation. In one embodiment, the gas flow rate can be in the range of 5 ml/sec to 50 ml/sec. The dielectric wall 210 can comprise a silicone material having a thickness ranging from a 0.005" to 0.015 and having a relative permittivity in the range of 3 to 4. The gas can be argon supplied in a pressurized cartridge which is commercially available. Pressure in the interior chamber 152 of dielectric structure 150 can be maintained between 14 psia and 15 psia with zero or negative differential pressure between gas inflow source 140A and negative pressure or vacuum source 145. The controller is configured to maintain the pressure in interior chamber in a range that varies by less than 10% or less than 5% from a target pressure. The RF power source 130A can have a frequency of 450 to 550 KHz, and electrical power can be provided within the range of 600 Vrms to about 1200 Vrms and about 0.2 Amps to 0.4 Amps and an effective power of 40 W to 100 W. In one method, the control unit 135 can be programmed to delivery RF energy for a preselected time interval, for example, between 60 seconds and 120 seconds. One aspect of a treatment method corresponding to the invention consists of ablating endometrial tissue with RF energy to elevate endometrial tissue to a temperature greater than 45 degrees Celsius for a time interval sufficient to ablate tissue to a depth of at least 1 mm. Another aspect of the method of endometrial ablation of consists of applying radiofrequency energy to elevate endometrial tissue to a temperature greater than 45 degrees Celsius without damaging the myometrium.

Figure 8D:
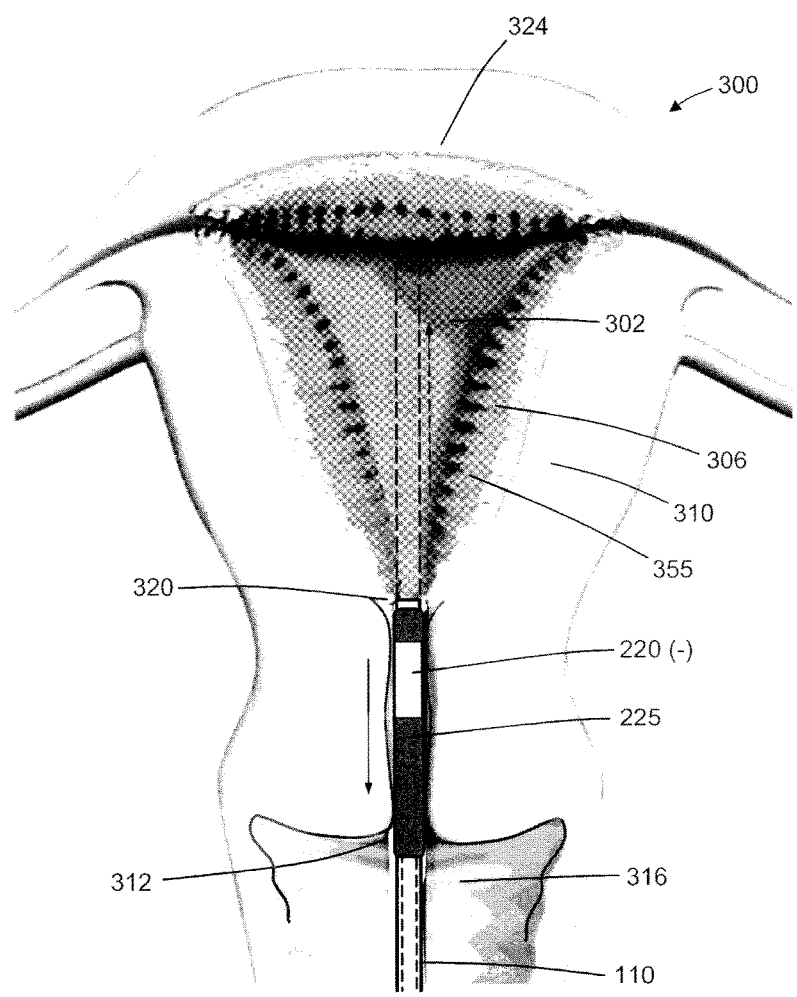
FIG. 8D is a schematic view of a subsequent steps of the method, including: (i) advancing the introducer sleeve over the thin-wall dielectric structure to collapse it into an interior bore shown in phantom view, and (ii) withdrawing the introducer sleeve and dielectric structure from the uterine cavity.

FIG. 8D illustrates a final step of the method wherein the physician deflates the expandable balloon member 225 and then extends sleeve 110 distally by actuating the handles 114a and 114b to collapse frame 155 and then retracting the assembly from the uterine cavity 302. Alternatively, the deployed working end 122 as shown in FIG. 8C can be withdrawn in the proximal direction from the uterine cavity wherein the frame 155 and thin-wall structure 150 will collapse as it is pulled through the cervix. FIG. 8D shows the completed ablation with the ablated endometrial tissue indicated at 360.

In another embodiment, the system can include an electrode arrangement in the handle 106 or within the gas inflow channel to pre-ionize the neutral gas flow before it reaches the interior chamber 152. For example, the gas inflow channel can be configured with axially or radially spaced apart opposing polarity electrodes configured to ionize the gas inflow. Such electrodes would be connected in separate circuitry to an RF source. The first and second electrodes 215 (+) and 220 (−) described above would operate as described above to provide the current that is capacitively coupled to tissue through the walls of the dielectric structure 150. In all other respects, the system and method would function as described above.

Figure 9:
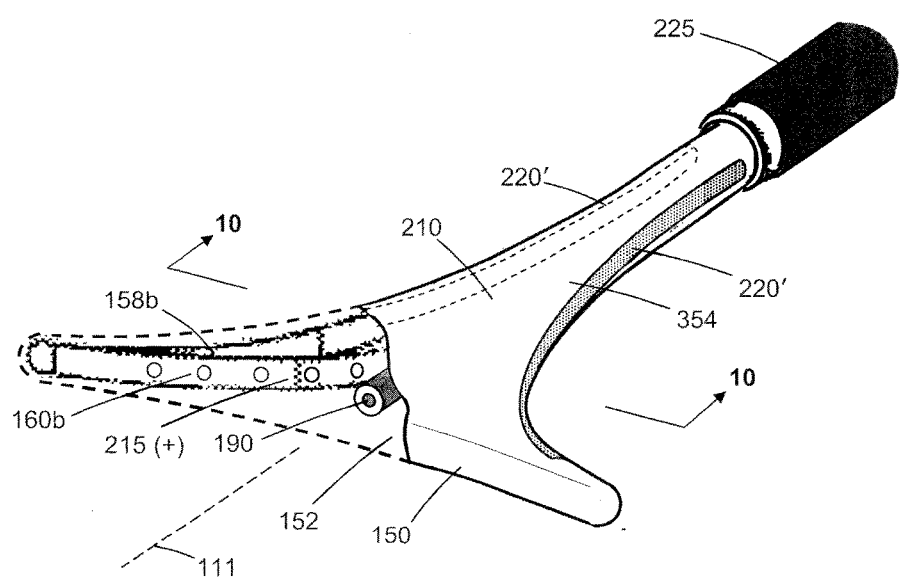
FIG. 9 is a cut-away perspective view of an alternative expanded thin-wall dielectric structure similar to that of FIGS. 5 and 6 show an alternative electrode configuration.
Figure 10:
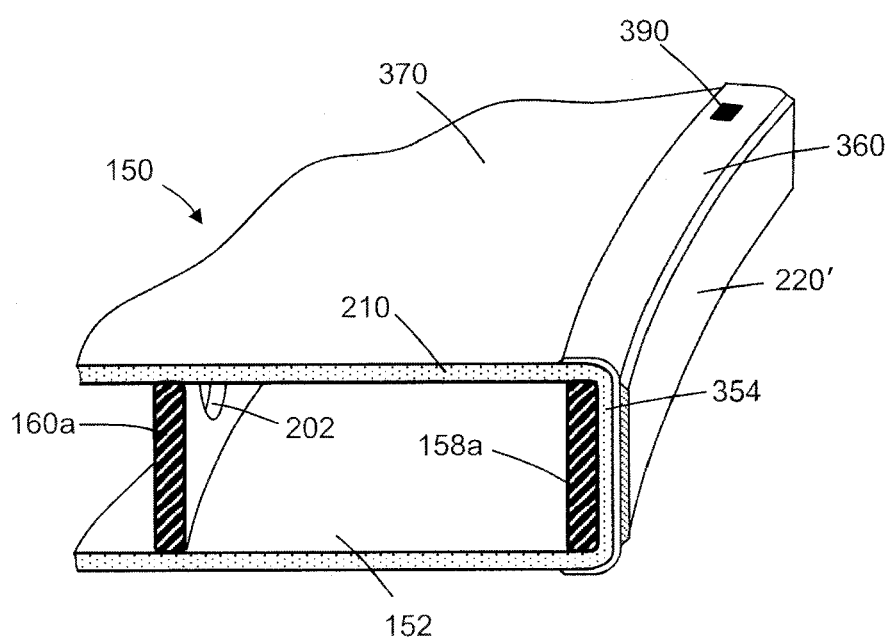
FIG. 10 is an enlarged cut-away view of a portion of the expanded thin-wall dielectric structure of FIG. 9 showing the electrode configuration.

Now turning to FIGS. 9 and 10, an alternate working end 122 with thin-wall dielectric structure 150 is shown. In this embodiment, the thin-wall dielectric structure 150 is similar to that of FIGS. 5 and 6 except that the second polarity electrode 220' that is exterior of the internal chamber 152 is disposed on a surface portion 370 of the thin-wall dielectric structure 150. In this embodiment, the second polarity electrode 220' comprises a thin-film conductive material, such as gold, that is bonded to the exterior of thin-wall material 210 along two lateral sides 354 of dielectric structure 150. It should be appreciated that the second polarity electrode can comprise one or more conductive elements disposed on the exterior of wall material 210, and can extend axially, or transversely to axis 111 and can be singular or multiple elements. In one embodiment shown in more detail in FIG. 10, the second polarity electrode 220' can be fixed on another lubricious layer 360, such as a polyimide film, for example KAPTON®. The polyimide tape extends about the lateral sides 354 of the dielectric structure 150 and provides protection to the wall 210 when it is advanced from or withdrawn into bore 120 in sleeve 110. In operation, the RF delivery method using the embodiment of FIGS. 9 and 10 is the same as described above, with RF current being capacitively coupled from the plasma 208 through the wall 210 and endometrial tissue to the second polarity electrode 220' to cause the ablation.

FIG. 9 further shows an optional temperature sensor 390, such as a thermocouple, carried at an exterior of the dielectric structure 150. In one method of use, the control unit 135 can acquire temperature feedback signals from at least one temperature sensor 390 to modulate or terminate RF energy delivery, or to modulate gas flows within the system. In a related method of the invention, the control unit 135 can acquire temperature feedback signals from temperature sensor 240 in interior chamber 152 (FIG. 6 to modulate or terminate RF energy delivery or to modulate gas flows within the system.

In another embodiment of the invention, FIGS. 11-14 depict systems and methods for evaluating the integrity of the uterine cavity which may be perforated or otherwise damaged by the transcervical introduction of probes and instruments into a uterine cavity. If the uterine wall is perforated, it would be preferable to defer any ablation treatment until the uterine wall is healed. A method of the invention comprises introducing transcervically a probe into a patient's uterine cavity, providing a flow of a fluid (e.g., $CO_2$) through the probe into the uterine cavity and monitoring the rate of the flow to characterize the uterine cavity as perforated or non-perforated based on a change in the flow rate. If the flow rate drops to zero or close to zero, this indicates that the uterine cavity is intact and not perforated. If the flow rate does not drop to zero or close to zero, this indicates that a fluid flow is leaking through a perforation in the uterine cavity 302 into the uterine cavity or escaping around an occlusion balloon that occludes the cervical canal.

Figure 11:
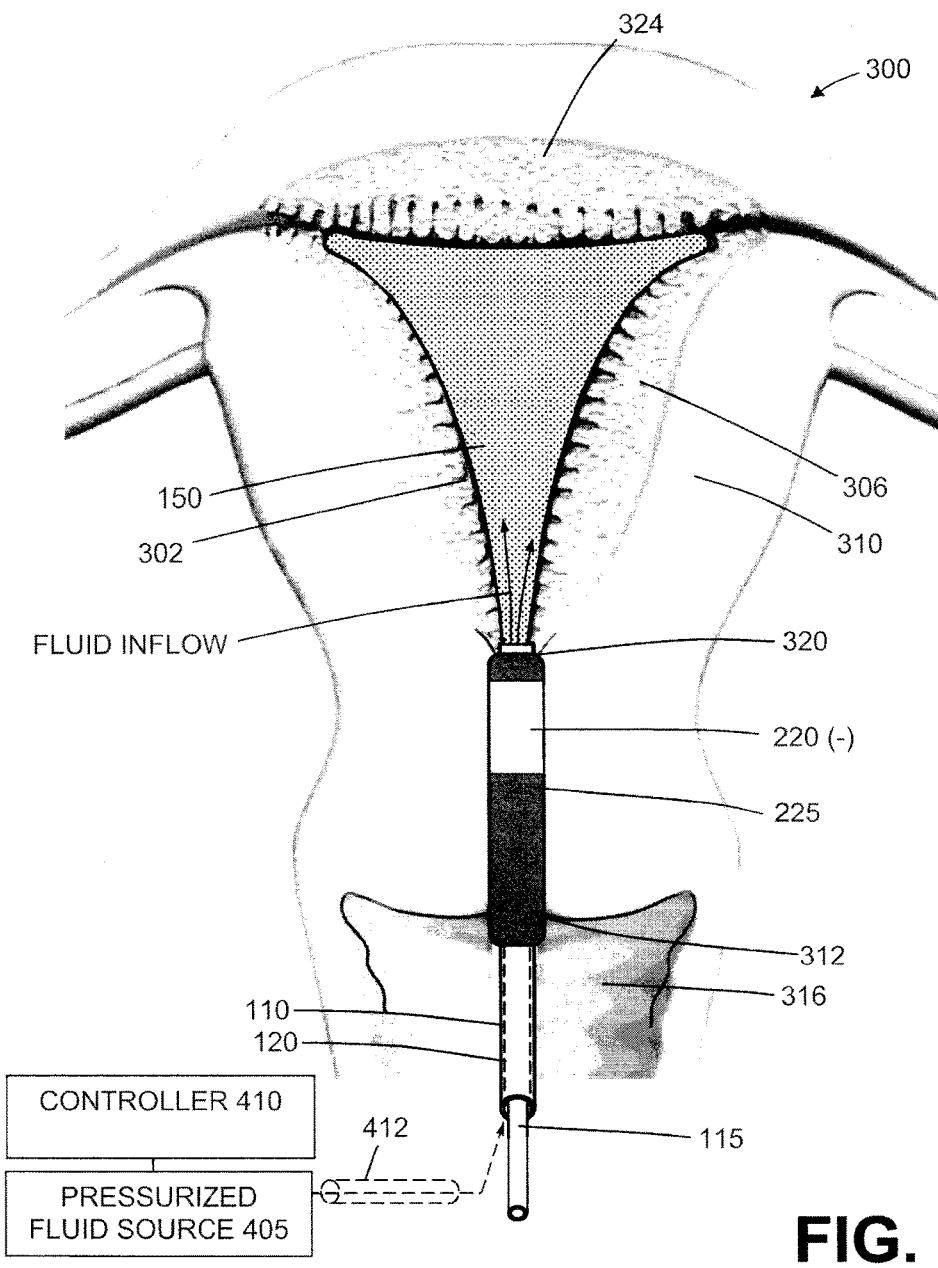
FIG. 11 is a schematic view of a patient uterus depicting a method corresponding to the invention including providing a flow of a fluid media into the uterine cavity and monitoring the flow rate to characterize the patient's uterine cavity as intact and non-perforated.
Figure 12:
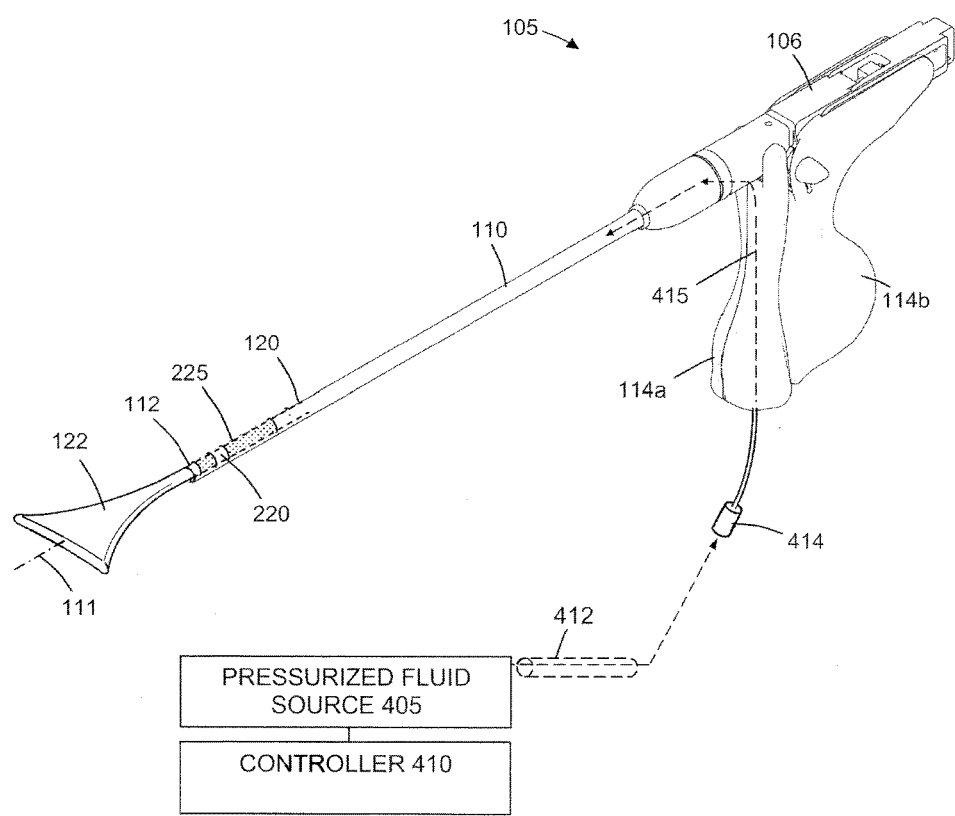
FIG. 12 is a perspective view of the ablation device of FIGS. 1-2 with a subsystem for checking the integrity of a uterine cavity.

In FIG. 11, it can be seen how a pressurized fluid source 405 and controller 410 for controlling and monitoring flows is in fluid communication with lumen 120 of introducer sleeve 110 (see FIG. 7). In one embodiment, the fluid source can be a pressurized cartridge containing $CO_2$ or another biocompatible gas. In FIG. 12, it can be seen that fluid source 405 communicates with a flexible conduit 412 that is connected to a "pig-tail" tubing connector 414 extending outward from handle 106 of the hand-held probe. A tubing in the interior of handle component 114a provides a flow passageway 415 to the lumen 120 in the introducer sleeve. In another embodiment, the fluid source 405 and flexible conduit 408 can be integrated into conduit 136 of FIG. 1.

In FIG. 11, it can be seen that the flow of fluid is introduced into the uterine cavity 302 after the balloon 225 in the cervical canal has been inflated and after the working end and dielectric structure 150 has been expanded into its triangular shape to occupy the uterine cavity. Thus, the $CO_2$ gas flows around the exterior surfaces of expanded dielectric structure 150 to fill the uterine cavity. Alternatively, the flow of $CO_2$ can be provided after the balloon 225 in the cervical canal is inflated but before the dielectric structure 150 is expanded.

Figure 13:
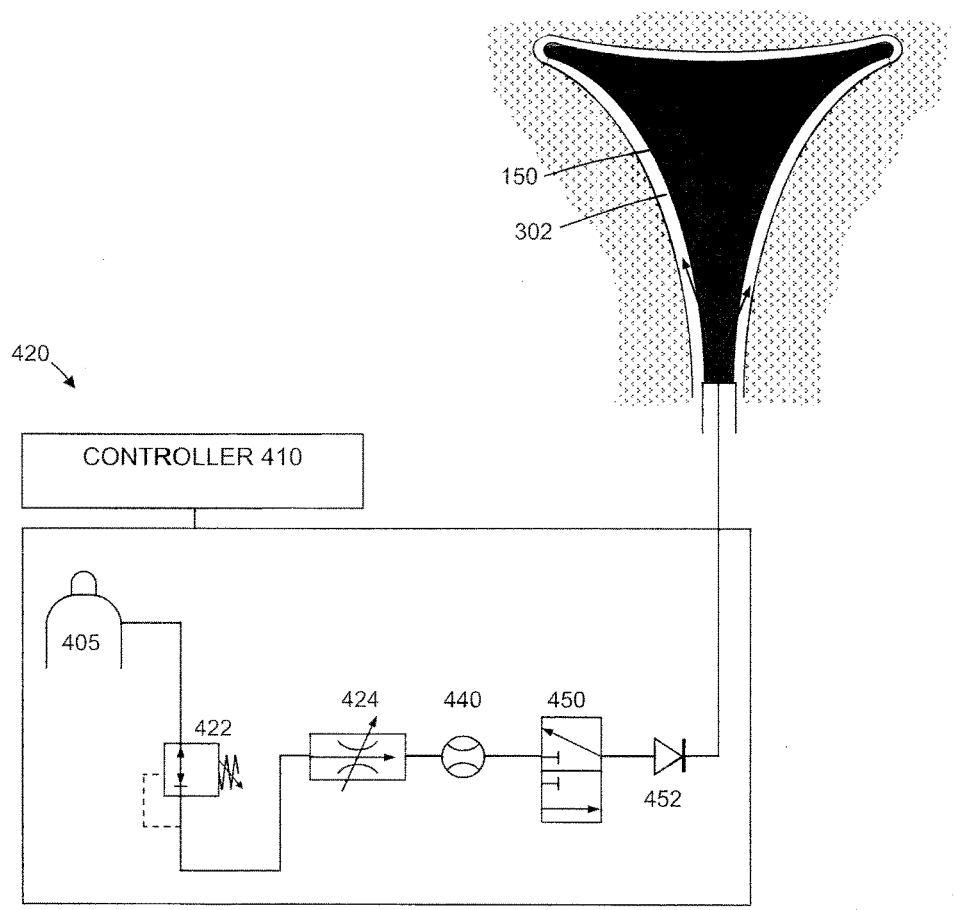
FIG. 13 represents a block diagram of a subsystem of the invention for providing and monitoring a fluid flow into the patient's uterine cavity.

FIG. 13 is a block diagram that schematically depicts the components of subsystem 420 that provides the flow of $CO_2$ to and through the hand-held probe 105. It can be seen that pressurized fluid source 405 communicates with a downstream pressure regulator 422, a proportional valve 424, flow meter 440, normally closed solenoid valve 450 and one-way valve 452. The valve 450 upon actuation by the system operator allows a flow of $CO_2$ gas from source 405 at a predetermined flow rate and pressure through the subsystem and into the uterine cavity 302.

In one embodiment of the method of operation, the physician actuates the system and electronically opens valve 450 which can provide a $CO_2$ flow through the system. The controller 410 monitors the flow meter or sensor 440 over an interval that can range from 1 second to 60 seconds, or 5 second to 30 seconds to determine the change in the rate of flow and/or a change in the rate of flow. In an embodiment, the flow sensor comprises a Honeywell AWM5000 Series Mass Airflow Sensor, for example Model AWM5101, that measure flows in units of mass flow. In one embodiment, the initial flow rate is between 0.05 slpm (standard liters per minute) and 2.0 slpm, or between 0.1 slpm and 0.2 slpm. The controller 410 includes a microprocessor or programmable logic device that provides a feedback signal from the flow sensors indicating either (i) that the flow rate has dropped to zero or close to zero to thus characterize the uterine cavity as non-perforated, or (ii) that the flow rate has not dropped to a predetermined threshold level within a predetermined time interval to thus characterize the uterine cavity as perforated or that there is a failure in occlusion balloon 225 or its deployment so that the cervical canal is not occluded. In one embodiment, the threshold level is 0.05 slpm for characterizing the uterine cavity as non-perforated. In this embodiment, the controller provides a signal indicating a non-perforated uterine cavity if the flow drops below 0.05 slpm between the fifth second of the flow and the flow time-out, which can be, for example, 30 seconds.

Figure 14:
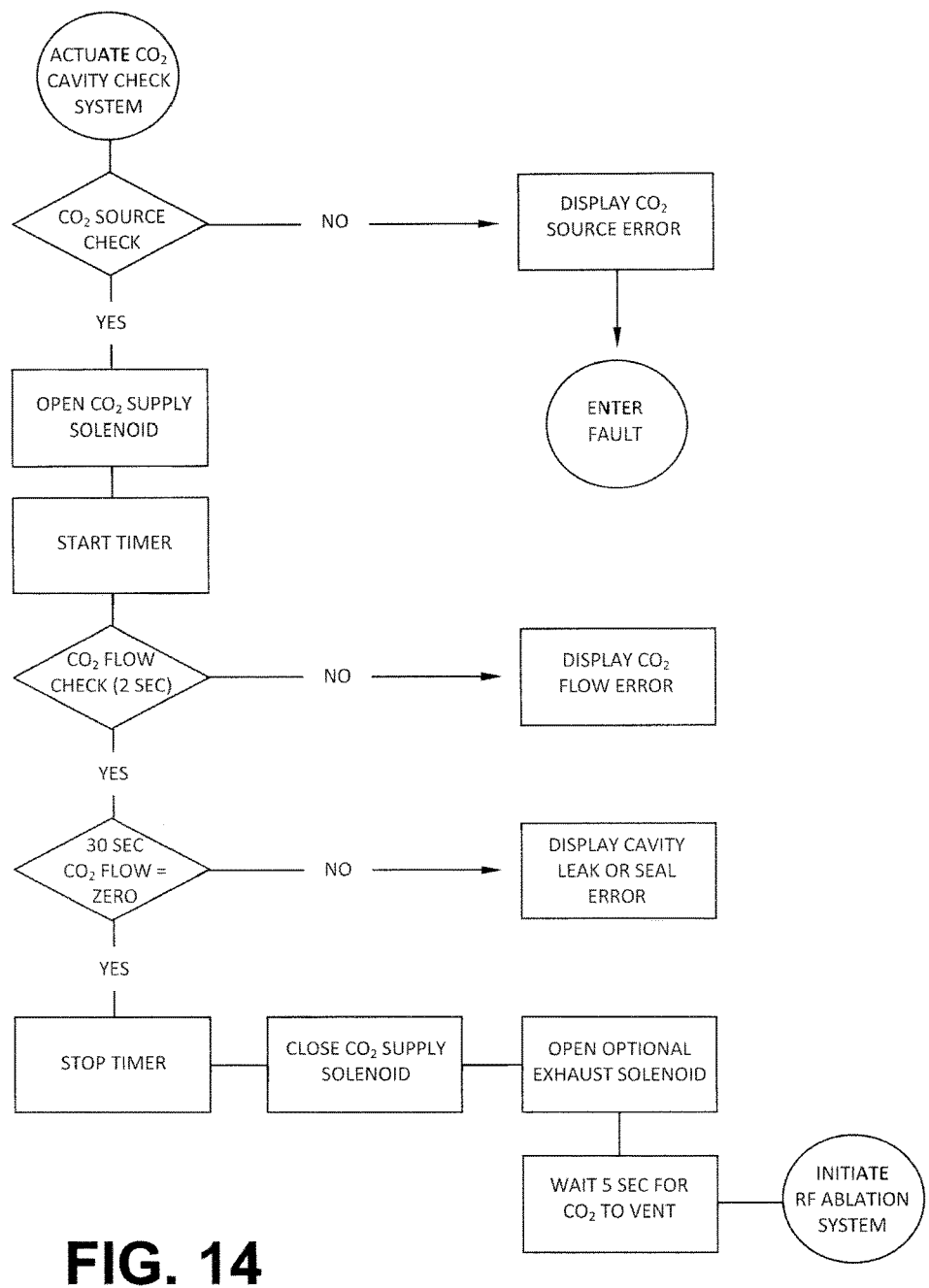
FIG. 14 represents a diagram indicating the steps of an algorithm for providing and monitoring a fluid flow into the patient's uterine cavity.

FIG. 14 depicts aspects of an algorithm used by controller 410 to accomplish a uterine cavity integrity check, with the first step comprising actuating a footswitch or hand switch. Upon actuation, a timer is initialized for 1 to 5 seconds to determine that a fluid source 405 is capable of providing a fluid flow, which can be checked by a pressure sensor between the source 405 and pressure regulator 422. If no flow is detected, an error signal is provided, such as a visual display signal on the control unit 135 (FIG. 1).

As can be understood from FIG. 14, after the fluid source 405 is checked, the controller opens the supply solenoid valve 450 and a timer is initialized for a 1 to 5 second test interval to insure fluid flows through the subsystem 420 of FIG. 13, with either or both a flow meter 440 or a pressure sensor. At the same time as valve 450 is opened, a timer is initialized for cavity integrity test interval of 30 seconds. The controller 410 monitors the flow meter 440 and provides a signal characterizing the uterine cavity as non-perforated if, at any time after the initial 5 second check interval and before the end of the timed-out period (e.g., the 30 second time-out), the flow rate drops below a threshold minimum rate, in one embodiment, to below 0.05 slpm. If the interval times out after 30 seconds and the flow rate does not drop below this threshold, then a signal is generated that characterizes that the uterine cavity is perforated. This signal also can indicate a failure of the occlusion balloon 225.

Referring to FIG. 14, in one embodiment, in response or otherwise as a result of the signal that the uterine cavity is not perforated, the controller 410 can automatically enable and activate the RF ablation system described above to perform an ablation procedure. The controller 410 can provide a time interval from 1 to 15 seconds to allow $CO_2$ gas to vent from the uterine cavity 302 before activating RF energy delivery. In another embodiment, the endometrial ablation system may include the optional subsystem 275 for exhausting fluids or gas from the uterine cavity during an ablation treatment (see FIG. 4 and accompanying text). This subsystem 275 can be actuated to exhaust $CO_2$ from the uterine cavity 302 which include opening solenoid valve 285 shown in FIG. 4.

The system can further include an override to repeat the cavity integrity check, for example, after evaluation and re-deployment of the occlusion balloon 225.

Figure 15:
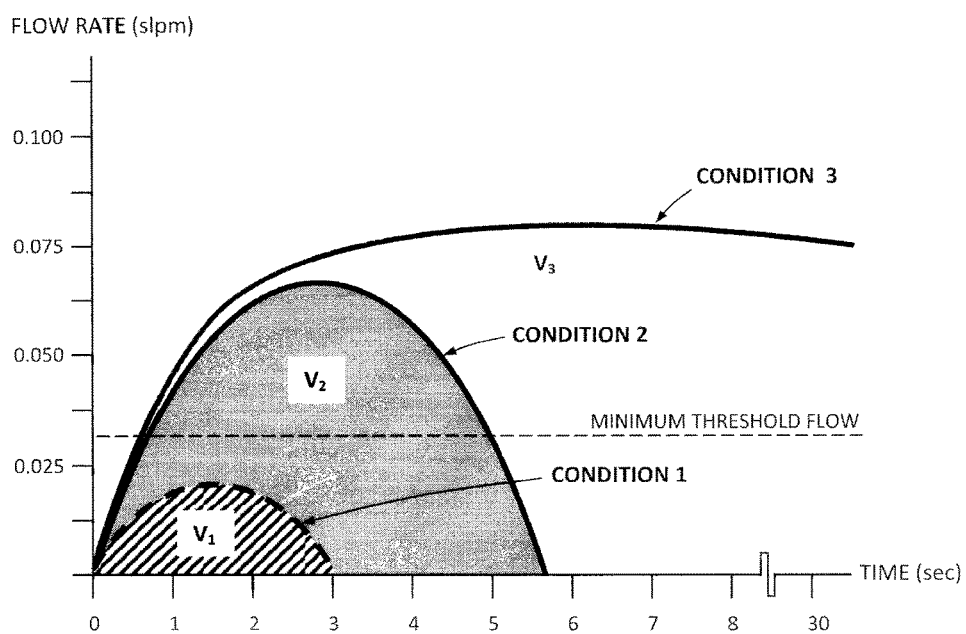
FIG. 15 is a chart illustrating gas flow rates into the uterine cavity over time that will result in three conditions to thereby characterize the uterine cavity as non-perforated or perforated.
Figure 16:
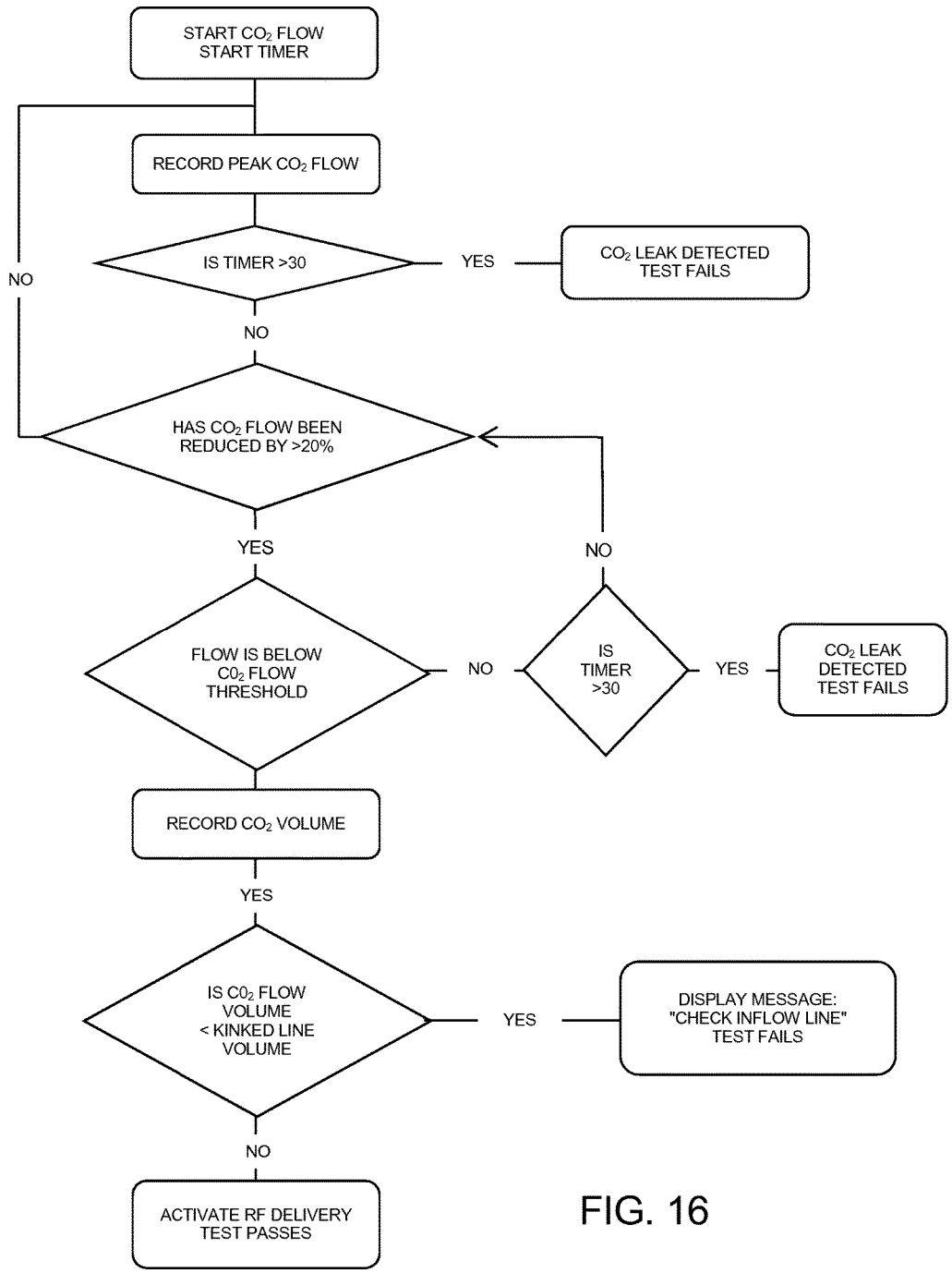
FIG. 16 represents a diagram indicating the steps of an algorithm for providing and monitoring a fluid flow related to the test method of FIG. 15.

FIGS. 15 and 16 represent another system and method for characterizing the uterine cavity as being non-perforated so as to safely permit an ablation procedure. This system and method utilizes variations in the algorithms that introduce a gas media fluid into the uterine cavity and thereafter measure the changes in flow rates in the gas media. The system again is configured to introduce a gas into the uterine cavity after deployment and expansion of an ablation device in the cavity. If the flow rate of the gas drops to approximately zero, this indicates that the uterine cavity is intact and not perforated. In the event the flow rate of the gas does not drop, there is likely a gas escaping from the uterine cavity 302 through a perforation in the uterine wall. Thus, the gas flow failing to drop may be an indication of a perforation.

FIG. 15 schematically illustrates three different conditions that may occur when operating the system, which indicate whether the system is functioning properly, and whether the uterine wall is non-perforated or perforated. In FIG. 15, the vertical axis indicates a gas flow rate measure in slpm (standard liters per minute), and the horizontal axis represents time in seconds. In one system variation, a gas source 405 such as a pressurized cartridge containing $CO_2$ is controlled by a controller 410, and the gas is introduced into the uterine cavity through a passageway in the device introducer sleeve 110 as described above (FIGS. 11-13). The controller 410 and flowmeter monitor flows from the device into the uterine cavity (FIG. 13). The initial flow rate can be in the range of 0.010 splm to 0.20 splm. In one aspect of the invention, a minimum flow rate has been found to be important as a system diagnostic check to insure gas flow is reaching the uterine cavity. Thus, FIG. 15 illustrates gas flow rate curve in a "condition 1" that may occur when the system fails in delivering gas through the passageways of the system. In one variation, the "condition 1" will be represented by a flow rate over time wherein the flow rate does not achieve a minimum threshold flow rate, which can be from 0.010 splm to 0.050 splm over a predetermined time interval. In one variation, the minimum flow rate is 0.035 splm. The time interval can be from 1 second to 15 seconds. This "condition 1" as in FIG. 15 could occur, for example, if the gas supply tubing within the device were kinked or pinched which would then prevent gas flow through the system and into the uterine cavity. In a related variation that indicates system failure, a controller algorithm can calculate the volume of gas delivered, and if the volume is less than a threshold volume, then a system failure or fault can be determined. The gas volume $V_1$ is represented by the "area under the curve" in FIG. 15, which is a function of flow rate and time.

FIG. 15 further illustrates a flow rate curve in a "condition 2" which corresponds to an intact, non-perforated uterine cavity. As can be understood from a practical perspective, a gas flow into an intact uterine cavity at a set pressure from a low pressure source, for example within a range of 0.025 psi to 1.0 psi, would provide an increasing flow rate into the cavity until the cavity was filled with gas, and thereafter the flow rate would diminish to a very low or zero flow rate. Such a "condition 2" flow rate curve as in FIG. 15 further assumes that there is an adequate sealing mechanism in the cervical canal. Thus, if controller obtains flow rate data from the flowmeter indicating "condition 2", then the patient's uterus is non-perforated and is suitable for an ablation. In operation, the controller can look at various specific aspects and parameters of the flow rate curve of "condition 2" in FIG. 15 to determine that the uterine cavity integrity test has passed, wherein such parameters can comprise any single parameter or a combination of the following parameters: (i) the flow rate falling below a threshold rate, for example between 0.010-0.10 splm; (ii) a change in rate of flow; (iii) a peak flow rate; (iii) the total gas volume $V_2$ delivered; (iv) an actual flow rate at a point in time compared to a peak flow rate; (v) a derivative of flow rate at a point in time, and (vi) any of the preceding parameters combined with a predetermined time interval. In one embodiment, a constant pressure (0.85 psi) gas is introduced and a minimum threshold flow is set at 0.035 splm. A peak flow is calculated after a time interval of 2 to 15 seconds, and thereafter it is determined if the flow rate diminished by at least 10%, 20%, 30%, 40% or 50% over a time interval of less than 30 seconds.

FIG. 15 next illustrates a flow rate curve in "condition 3" which represents a gas flow when there is a perforated wall in a uterine cavity, which would allow the gas to escape into the abdominal cavity. In FIG. 15, a gas flow at a constant pressure is shown ramping up in flow rate until it levels off and may decline but not the rate of decline to may not go below a threshold value or may not decline a significant amount relative to a peak flow rate. Such a flow rate curve over time would indicate that the gas is leaking from the uterine cavity.

Now turning to FIG. 16, an algorithm diagram is shown that describe one variation in a method of operating a uterine cavity integrity test based on measuring gas flow rates over a selected time interval. At the top of the diagram, the physician actuates the system in which a valve 450 is opened to provide a $CO_2$ flow through the system (FIG. 14). The controller 410 provides a flow at a pressure, for example 0.85 psi. The actuation of the system also starts a timer wherein a first interval is 30 seconds or less. Over this 30-second interval, the controller records the peak flow rate which typically can occur within 2 to 10 seconds, then monitors the flow rate over the remainder of the 30 second interval and determined whether the flow rate drops 20% or more from the peak flow rate. Then, the controller additionally monitors whether the flow rate falls below a threshold value, for example 0.035 splm. If these two conditions are met, the test indicates that there is no leakage of gas media from the uterine cavity. If the flow rates does not drop 20% from its peak with 30 seconds together with flow being below threshold value, then the test fails indicating a leak of gas from the uterine cavity. Thereafter, the diagram in FIG. 16, indicates one additional test which consists of calculating the volume of gas delivered and comparing the volume to the maximum volume within a kinked gas delivery line. If the delivered gas volume is less than the capacity of the gas delivery line, then the test fails and the signal on the controller can indicate this type of test failure. If the delivered gas volume is greater than the capacity of a gas delivery line, then the test passes. In one variation of the controller algorithm can then automatically actuate the delivery of RF energy in an ablation cycle. Alternatively, the controller can provide a signal that the test has passed, and the physician can manually actuate the RF ablation system.

Figure 17:
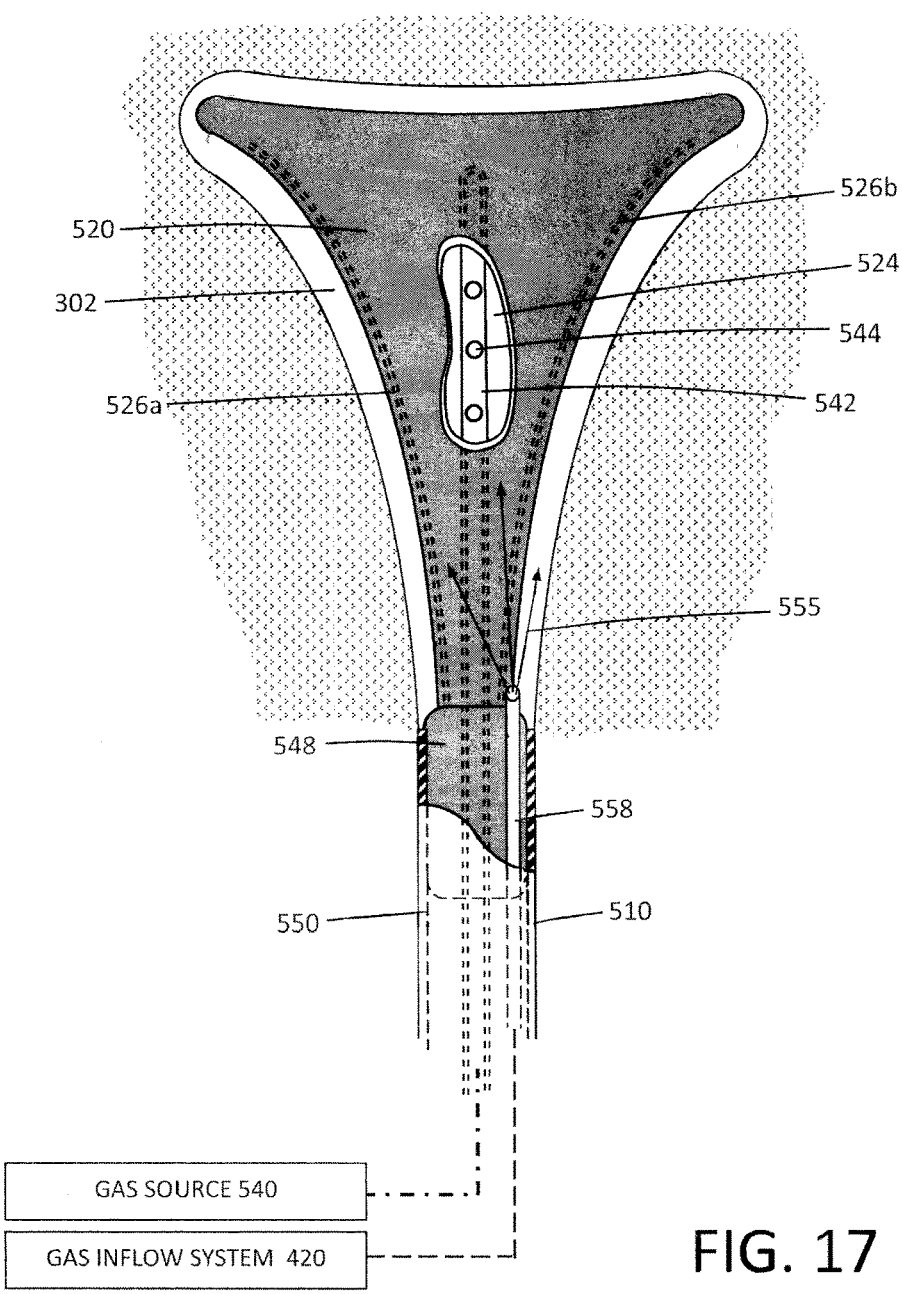
FIG. 17 is a schematic view of another system and method for providing and monitoring a fluid flow to characterize the integrity of a uterine cavity.

FIG. 17 schematically illustrates another system and method for characterizing integrity of the walls of a uterine cavity. As can be seen in FIG. 17. an introducer sleeve 510 carrying an expandable working end 520 is deployed in the uterine cavity 302. The working end includes a balloon-like member 522 with a fluid-tight interior chamber 524. In one embodiment, the working end 510 is expanded laterally by frame elements 526a and 526b, which is similar to previously described embodiments. In addition, a pressurized gas source 540 is actuated to provide an inflation gas through interior sleeve 542 and ports 544 therein that further expands and opens the working end 520 transverse to opening forces applied by frame elements 526a and 526b. The inflation gas can comprise an argon gas that later is converted to a plasma as described previously. The inflation gas can pressurize the working end to a selected pressure ranging from 0.10 psi to 10 psi. In one variation, the pressure can be 0.50 psi.

As can be seen in FIG. 17, an expandable member 548 or balloon is expanded to prevent any gas flow outwardly through the bore 550 in introducer sleeve 510. Thereafter, a gas inflow system 410 similar to that of FIG. 13 is utilized to flow a gas source, such as $CO_2$ into the uterine cavity 302 (FIG. 17). In FIG. 17, the gas inflow is indicated by arrows 555 which can comprise an inflow at a predetermined pressure through passageway 558 as described above, and in one variation can be 0.85 psi. The test for uterine cavity integrity then can monitor one or more gas leakage parameters relating to the inflation gas in the interior chamber 524 of the working end 520. For example, the flow into the uterine cavity 302 will cause an outflow of gas from the interior chamber 524 through passageway 558 which can be measure by a flow meter, or the volume of gas outflow can be measured or the change in gas pressure can be measured. If there is no leak in the uterine cavity, the parameter of the inflation can in the interior chamber 524 will reach an equilibrium in relation to the $CO_2$ inflow into the cavity. If the inflation gas parameter does not reach an equilibrium, then the change in parameter (flow, volume or pressure) will indicate a leakage of gas from the uterine cavity through a perforation. In general, a method of characterizing the integrity of a patient's uterus comprises positioning a probe working end is a patient's uterine cavity, the working end comprising an inflated resilient structure, introducing a flow of a gas through the probe into a uterine cavity exterior about the exterior of the working end, and measuring a gas flow, gas volume or gas pressure parameter of the inflation media in the inflated resilient structure in response to the gas flow into the uterine cavity.

Figure 18:
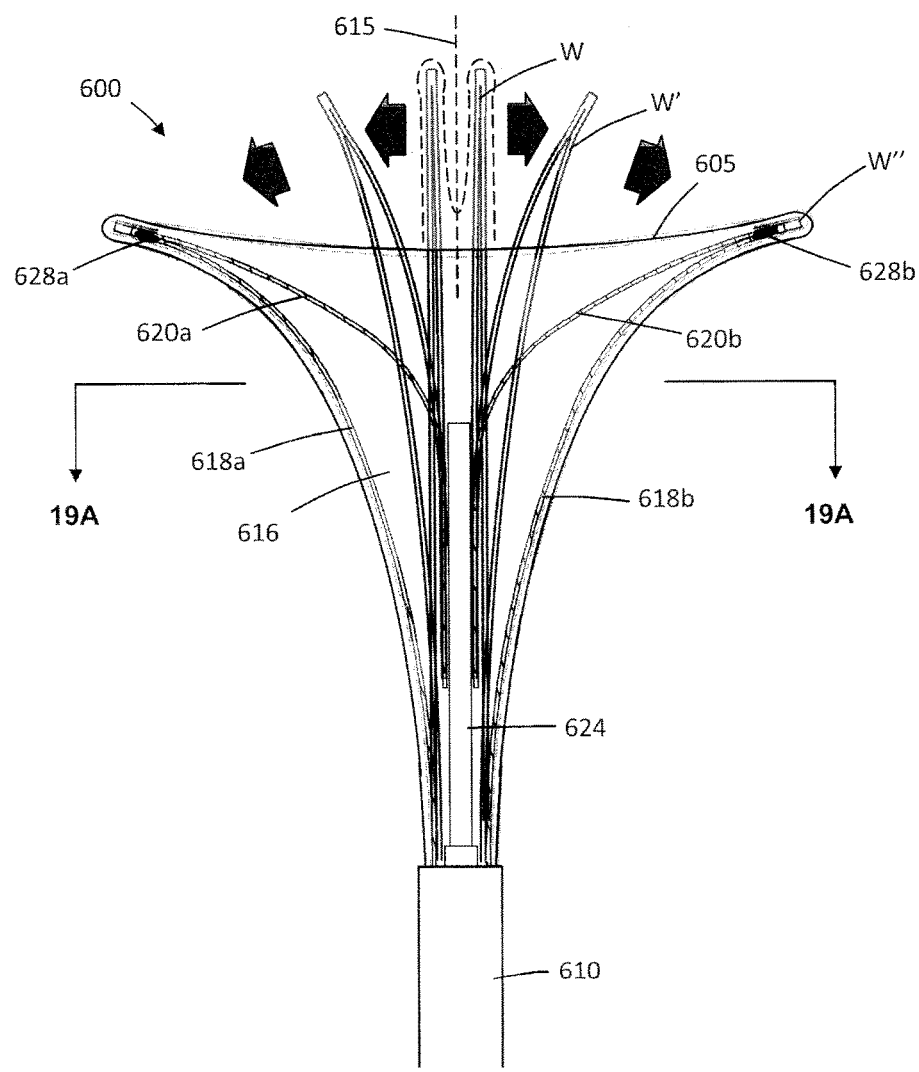
FIG. 18 is a schematic view of another system working end of the invention illustrating expansion of the dielectric membrane in a lateral directions with an interior frame.
Figure 19A:
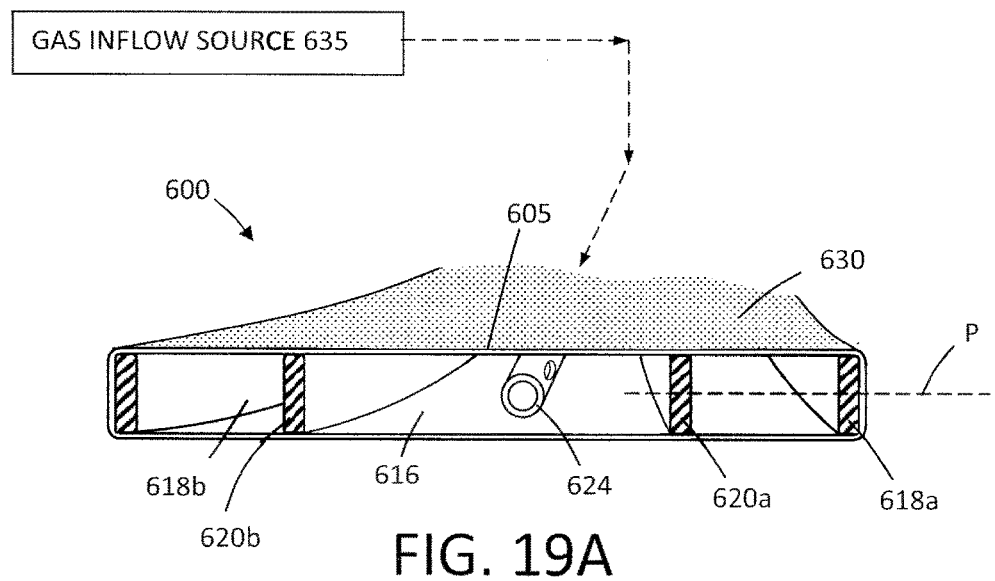
FIG. 19A is a sectional view of the working end of FIG. 18 taken along line 19A-19A with the dielectric membrane expanded in lateral directions by the interior frame.
Figure 19B:
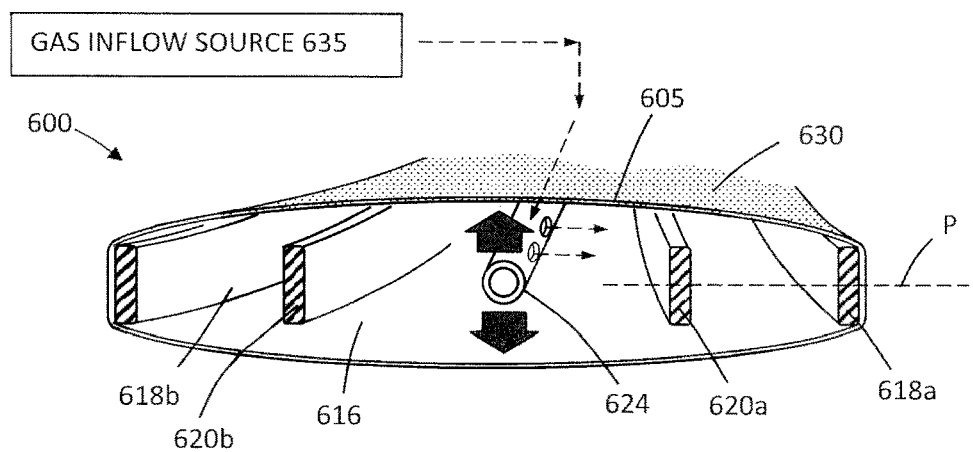
FIG. 19B is a sectional view of the working end of FIG. 19A showing expansion of the dielectric membrane with an inflation medium to expand the membrane in a second direction.

FIGS. 18 and 19A-19B schematically illustrates another embodiment of working end 600 and a method of use. FIG. 18 is a plan view of an expandable dielectric member or membrane 605 carried at distal end of introducer 610 that extend along longitudinal axis 615. The working end 600 is similar to previously described embodiments, which includes an expandable-collapsible frame of a spring material within a fluid-tight interior chamber 616 of an elastic dielectric member 605. In one embodiment the frame comprises flexible outward frame elements 618a and 618b that can bowed outwardly from shape have width W to a shape with width W' to fully expanded width W" as shown in FIG. 18. The outward frame elements 618a and 618b are flexed by distal movement of inner frame elements 620a and 620b that are coupled at proximal ends 622a and 622b to slidable inner sleeve 624. It can be understood from FIG. 18 that the distal tips of inner frame elements 620a and 602b are welded to distal tips of outward frame elements 618a and 618b, respectively as indicated by welds 628a and 628b. The frame elements are thus configured to provide lateral expansion forces to expand the dielectric member 605 and its ablation surface 630 (FIG. 19A) laterally relative to axis 615.

FIGS. 19A-19B illustrates another aspect of the invention wherein the working end 600 and more particularly the dielectric member 605 can be expanded in a second direction relative to axis 615 that is transverse to the plane P of the frame expansion. FIG. 19A shows the dielectric membrane 605 stretched and expanded laterally by the frame elements as in FIG. 18. FIG. 19B shows the dielectric membrane 605 further expanded by inflation of the interior chamber 616 by means of a pressurized inflow of gas from a gas inflow source 635 that is in communication with the interior chamber. In one embodiment, the gas flow into the dielectric member 605 comprises the Argon gas inflow that is ionized as described previously to enable the electrosurgical energy delivery aspects of the invention.

Referring to FIG. 19B, it has been found that positive pressure in the interior chamber 616 during operation is useful in ablating tissue since the positive pressure can help in maintaining the ablation surface 630 in contact with tissue, which in turn permits more effective capacitive coupling through the dielectric membrane 605 and passive heating from the membrane when heated by ion bombardment. In one embodiment, the pressure in the balloon is at least 20 mm Hg, at least 30 mm Hg, at least 40 mm Hg or at least 50 mm Hg. Since the Argon gas is circulating as described above, the gas inflow rate and gas outflow rate can be modulated with valve assemblies to provide a net positive pressure in the interior chamber. It also has been found that positive pressure in the interior chamber 616 can be useful in causing plasma filaments to be more uniform and more widely dispersed since the dielectric membrane is spaces away from the frame elements 620a and 620b in the central region of the interior chamber.

In another aspect of the invention, the gas pressure in the interior chamber 616 of the dielectric membrane 605 can be modulated during the initiation and duration of a treatment cycle. In one variation, the pressure in the interior chamber prior to actuating RF delivery can be lowered to less than ambient pressure. At the time of RF actuation, the lower Argon pressure will permit more instantaneous ignition of the plasma due to such lowered pressure. Since the Argon gas is circulating, the gas inflow and outflow rates can be modulated with the valve subsystems to provide a negative pressure in interior chamber 616. The pressure can be at least 5% below ambient pressure, at least 10% below ambient pressure, at least 15% below ambient pressure, or at least 20% below ambient pressure. After ignition of plasma in the interior chamber 616, the pressure can be regulated to a higher pressure as described above to expand the dielectric membrane away from the frame elements 620a and 620b.

Figure 20:
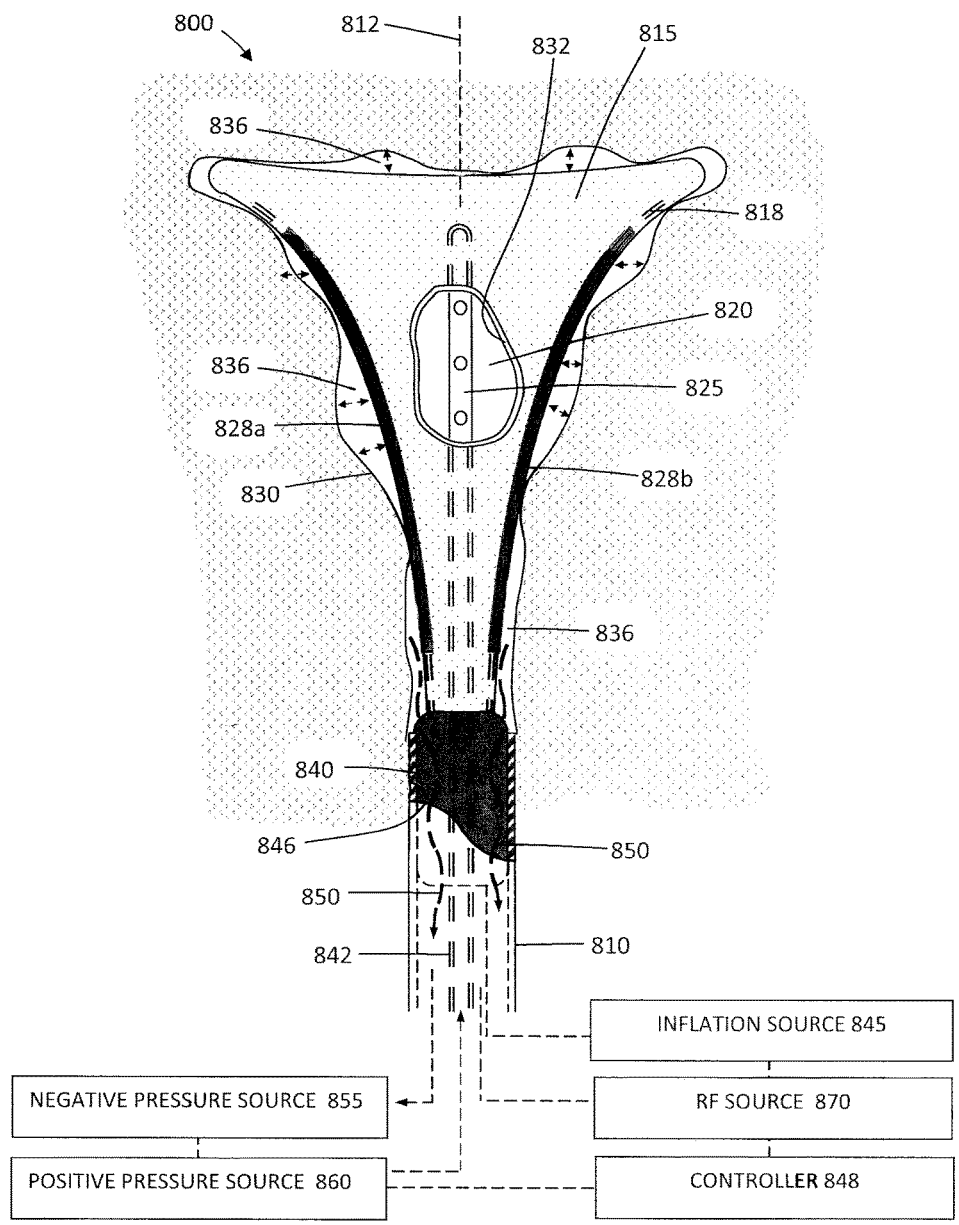
FIG. 20 is a cut-away view of another working end showing the dielectric membrane and a valve system for releasing pressure from the uterine cavity during an ablation cycle.

FIG. 20 illustrates another embodiment of an endometrial ablation system 800 with an elongated sleeve 810 having axis 812 and carrying expandable dielectric structure 815 that is expanded by a frame 818 in an interior chamber 820 of the dielectric. The system operates to apply ablative energy to endometrial tissue as described previously with a first polarity electrode 825 in the interior chamber 820 of the dielectric and second polarity electrodes 828a, 828b on the exterior of the dielectric 815. Plasma is formed in the interior chamber 820 which allows capacitive coupling of RF current across dielectric wall 832 which thus causes tissue heating as described previously. The embodiment of working end depicted in FIG. 20 is configured to allow steam and/or fluid media to escape from the uterine cavity 830 during a treatment cycle if pressure exceeds a predetermined level. It has been found that the surface of silicone wall 832 can intermittently generate steam within the cavity 830 which will locally push the uterine wall out of contact with the dielectric structure 815. FIG. 20 depicts the dielectric structure 815 expanded in the uterine cavity during an ablation cycle wherein pockets or regions 836 are created by steam expansion around the cavity (see arrows in regions 836). In FIG. 20, an inflatable balloon 840 is disposed in the distal end of sleeve 810 to function as a relief valve. The balloon 840 has an annular configuration and surrounds the axial-extending member 842 that carries the frame 818 and the dielectric structure 815. The balloon 840 can have any suitable axial length ranging from about 5 mm to 5 cm. The inflatable valve balloon 840 is in communication with an inflation source 845 and controller 848 for expanding the balloon in lumen 846 of sleeve 810. The balloon 840 is controlled at a pressure ranging from 10 mmHg to 100 mmHg in the interior chamber of the valve balloon 840. In one variation, the balloon 840 is inflated to a pressure of between 25 to 50 mmHg, and during a treatment cycle, transient steam pockets 836 may form and the increase in uterine cavity pressure compresses the balloon 840 and permits fluid media to escape around the balloon into lumen 846 as indicated by arrows 850 (FIG. 20). The lumen 846 in sleeve 810 is configured to direct any escaped fluid media in the proximal direction to vent or collect such fluid. The fluid pathway can further include an aspiration or negative pressure source coupled to lumen 846 (FIG. 20). In this embodiment, the valve balloon 840 is independent of the fluid-tight dielectric structure 815 which also can be characterized as a balloon. The surface of balloon 840 and the surface of lumen 846 can be designed to cooperate in sealing the lumen 846 at low pressure and then functioning at a relief valve at a predetermined higher pressure. For example, the interior surface of the lumen 846 can be configured with annular or axial ridges that cooperate with the modulus and wall thickness of the valve balloon 840. Also, the sleeve lumen 846 can have a hydrophilic or hydrophobic surface to provide a releasable sealing effect against the balloon 840. Likewise, the surface of balloon 840 can be configured with annular or axial ridges that cooperate a smooth lumen wall or a grooved lumen wall. Also, the balloon can have a hydrophilic or hydrophobic surface to provide the desired releasable sealing effect. As can be seen in FIG. 20, the system provides positive and negative pressure sources, 855 and 860, to circulate a neutral gas such as Argon through the interior chamber 820 of the dielectric 815 as described previously. The RF source 870 and controller 848 also operate as described previously to generate plasma within the dielectric 815 and to apply energy to tissue through the dielectric.

Figure 21:
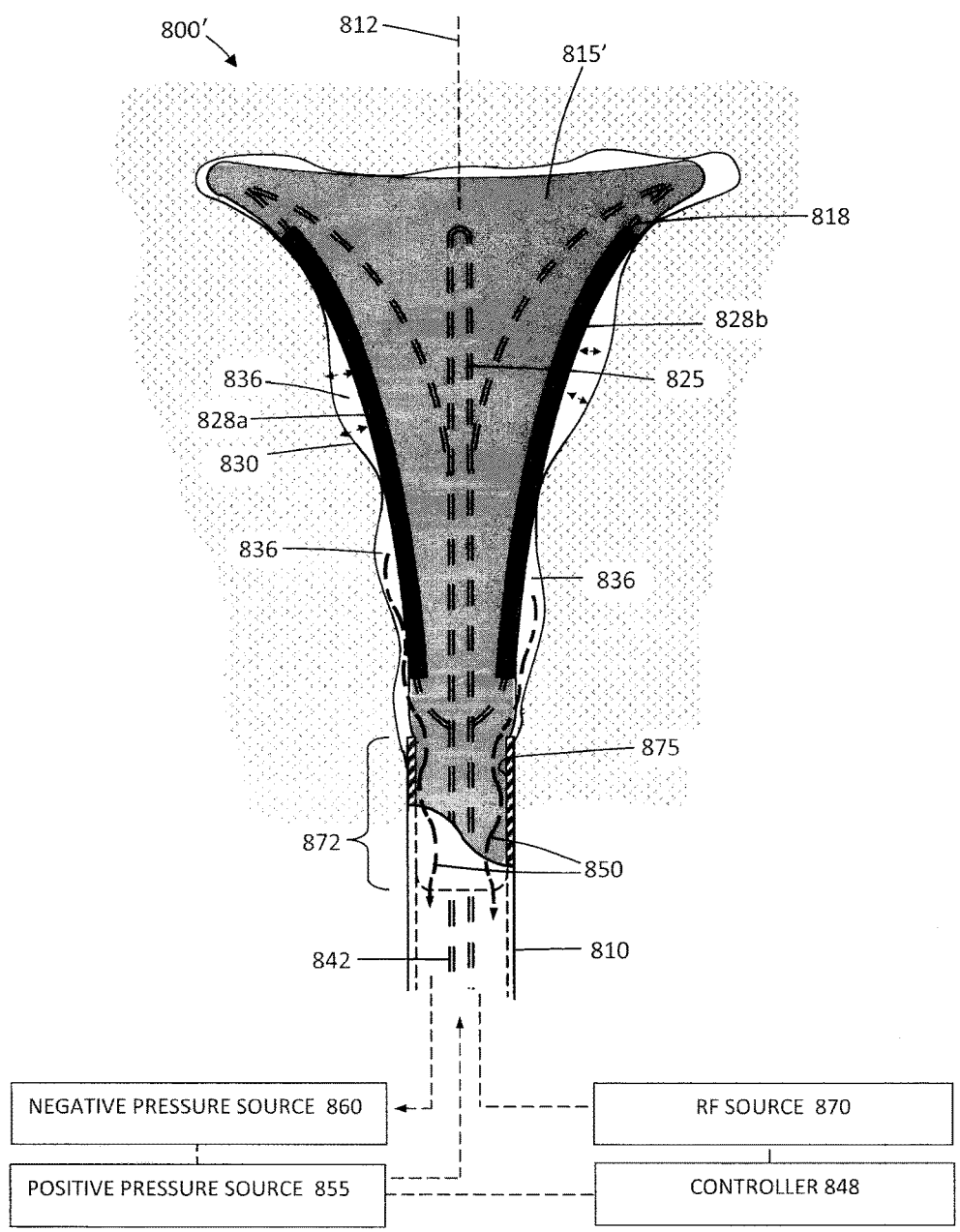
FIG. 21 depicts an alternative working end showing the dielectric membrane that functions as a valve system for releasing pressure during an ablation cycle.

FIG. 21 illustrates another system embodiment 800' for endometrial ablation in which elongated sleeve 810 carries an expandable dielectric structure 815' that again is expanded laterally by frame 818 in interior chamber 820 of the dielectric. The system utilizes an RF electrode 825 in interior chamber 820 and opposing polarity electrodes 828a, 828b on the exterior of the dielectric 815 as described previously to allow capacitive coupling of RF current across dielectric wall 832. The embodiment of FIG. 21 uses positive and negative pressure sources 855 and 860 to circulate a neutral gas through interior chamber 820 and control pressure in the fluid-tight interior chamber 820 of the dielectric 815' during a treatment cycle. As can be seen in FIG. 21, the proximal portion 872 of the inflatable dielectric 815' extends into lumen 875 of sleeve 810. Thus, the proximal portion 872 of dielectric 815' can function as a balloon valve as described in the embodiment of FIG. 20 to allow steam and/or fluid media to escape from the uterine cavity 830 during a treatment cycle if pressure exceeds a predetermined level. In the embodiment of FIG. 21, the system parameters for plasma generation are adapted to provide a pre-determined pressure (e.g., 50 mmHg) for releasing pressure from the uterine cavity. FIG. 21 depicts vapor/fluid escape from the uterine cavity along arrows 850 from transient vapor pockets 836. In all other respects, the embodiment of FIG. 21 functions as the embodiment of FIG. 20. The advantage of the system embodiment 800' of FIG. 21 is that a single expandable member 815' functions the ablation structure and the balloon valve. This aspect of the invention reduces complexity and eliminates the need for independent inflation source 845 for inflating an independent balloon valve.

Figure 22:
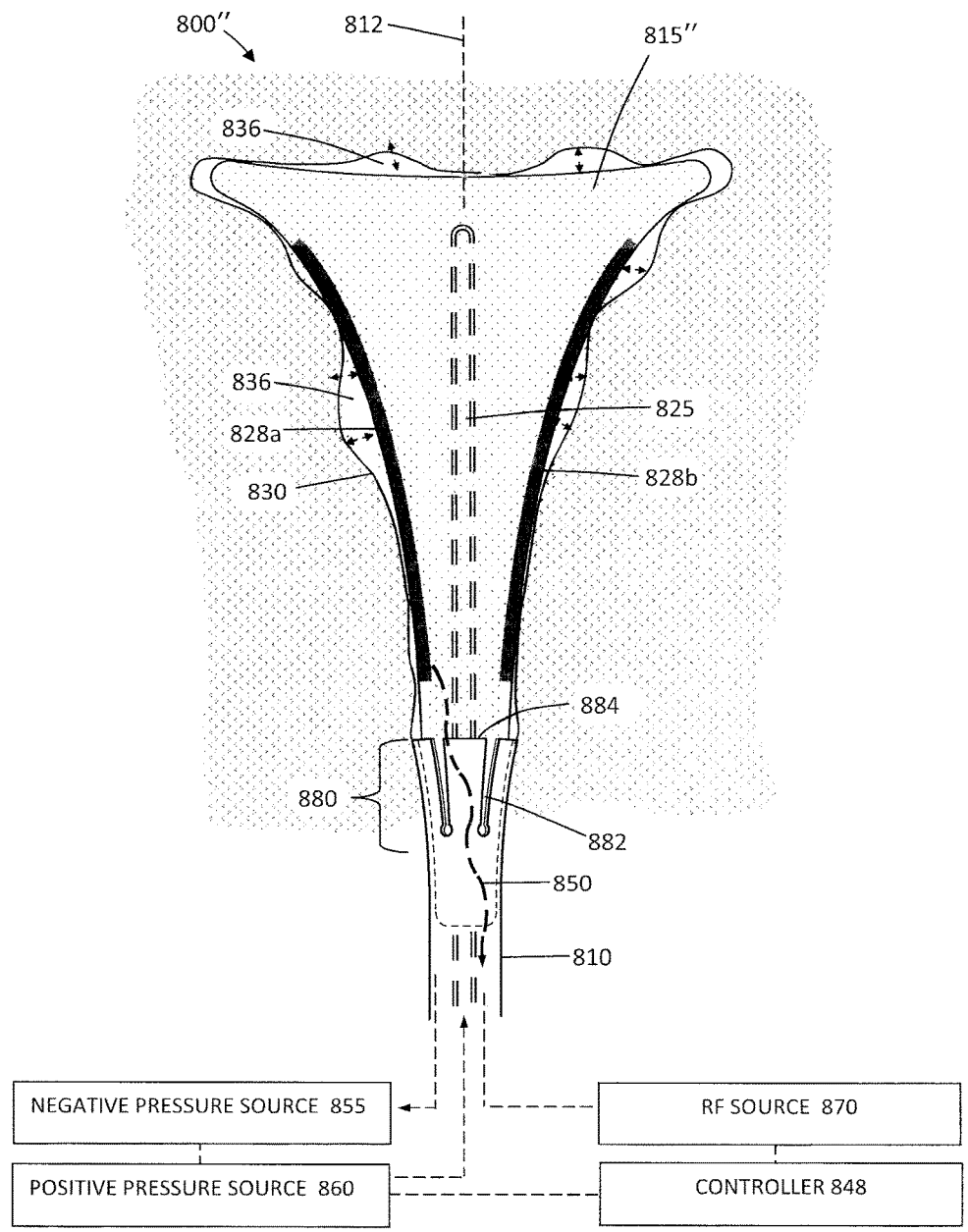
FIG. 22 is another working end embodiment showing an introducer sleeve with a flexible distal end portion.
Figure 23:
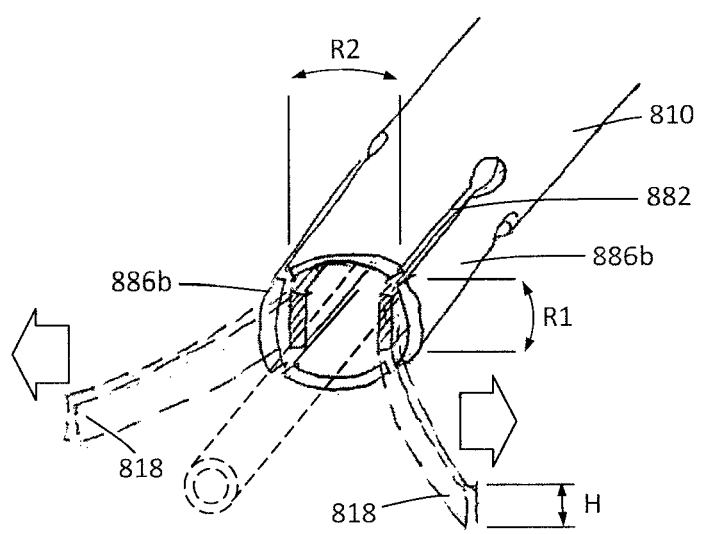
FIG. 23 is another view of the flexible distal end portion of the introducer sleeve of FIG. 22.

FIGS. 22 and 23 illustrates another system embodiment 800" for endometrial ablation. In this embodiment, the distal end portion 880 of sleeve 810 includes a plurality of slots 882 which allow the end portion 880 to flex outward to provide a larger cross section when the expandable dielectric structure 815" is expanded. The slots 882 can extend axially and have a length of from about 5 mm to 25 mm. The flexibility of the distal end portion 880 reduces the risk of the distal edge 884 cutting the elastomeric wall 832 of the dielectric structure after its expansion. The slots 882 can range in number from one to 10 or more and can be symmetric or asymmetric around the sleeve. FIG. 23 shows one variation in which the slots 882 are asymmetric and are configured to cooperate with the height dimension H of the laterally-expandable frame 818. It can be seen that radial angle R1 is less than radial angle R2 and in use the lateral elements 886a and 886b would flex outward upon expansion of the frame 818 and dielectric structure 815". In one embodiment, the height H of the frame is about 2.5 to 3.0 mm and the diameter of the sleeve 810 is from 6 mm to 8 mm. The distal end portion 880 of the sleeve 810 also can be covered with a thin wall elastomer to cover the slots 882 (not shown) which permits outward flexing under expansion of the dielectric to provide further protection of the dielectric structure. Referring to FIG. 22, the dielectric structure 815" can extend proximally a distance of 5 to 20 mm proximal from the slots 882 to permit the dielectric to function as a valve as in the embodiment of FIG. 21. In FIG. 22, vapor or fluid media is indicated at 850 escaping around the inflated dielectric 815".

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An electrosurgical ablation probe comprising:
    a shaft having a proximal end, a distal end, and a gas flow passage with an opening near a distal end of the shaft;
    a dielectric wall having an interior surface, an exterior surface, and an interior volume carried at the distal end of the shaft;
    a barrier element in the flow passage, said barrier configured to open when a gas pressure in the interior volume is less than a predetermined pressure and close when said gas pressure in the interior volume is greater than the predetermined pressure;
    a first electrode structure disposed within said interior volume; and
    a second electrode structure disposed on the exterior surface of the dielectric wall;
    said first and second electrodes configured to be connected to a source of a radiofrequency voltage to initiate a plasma in an electrically non-conductive gas flowing through the interior volume of the dielectric wall when tissue contacts the exterior surface of the dielectric wall and establishes a current path between the first and second electrodes through the plasma, dielectric wall, and tissue.

2. An electrosurgical ablation probe as in claim 1, wherein the barrier element is disposed in a distal end of the gas flow passage.

3. An electrosurgical ablation probe as in claim 1, wherein the barrier element is a balloon structure which is inflatable independently of the interior volume of the dielectric wall.

4. An electrosurgical ablation probe as in claim 3, wherein the barrier element comprises a proximal portion of the dielectric wall.

5. An electrosurgical ablation probe as in claim 3, further comprising an inflation source coupled to deliver an inflation medium to the barrier element.

6. An electrosurgical ablation probe as in claim 5, wherein the inflation source is adapted to inflate the barrier element at a pressure in the range from 10 mm Hg to 100 mm Hg.

7. An electrosurgical ablation probe as in claim 5, wherein the inflation source is adapted to inflate the barrier element at a pressure in the range from 25 mm Hg to 75 mm Hg.

* * * * *